(12) United States Patent
Ramella-Roman et al.

(10) Patent No.: US 8,308,299 B2
(45) Date of Patent: Nov. 13, 2012

(54) LENSLET ARRAY FOR RETINAL OXIMETRY

(75) Inventors: Jessica C. Ramella-Roman, Washington, DC (US); Scott A. Mathews, Germantown, MD (US); Mark Mirotznik, Silver Spring, MD (US)

(73) Assignee: The Catholic University of America, Washington, DC (US)

( * ) Notice: Subject to any disclaimer, the term of this patent is extended or adjusted under 35 U.S.C. 154(b) by 6 days.

(21) Appl. No.: 13/177,742

(22) Filed: Jul. 7, 2011

(65) Prior Publication Data

US 2011/0261321 A1 Oct. 27, 2011

Related U.S. Application Data

(62) Division of application No. 12/262,696, filed on Oct. 31, 2008, now Pat. No. 7,997,732.

(60) Provisional application No. 61/102,947, filed on Oct. 6, 2008.

(51) Int. Cl.
- *A61B 3/00* (2006.01)
- *A61B 3/14* (2006.01)
- *A61B 3/10* (2006.01)
- *G02B 27/10* (2006.01)

(52) U.S. Cl. ......... 351/246; 351/206; 351/213; 359/619

(58) Field of Classification Search .......... 359/618–619, 359/601; 351/206, 213, 246; 600/310
See application file for complete search history.

(56) References Cited

U.S. PATENT DOCUMENTS

| | | | |
|---|---|---|---|
| 4,541,697 A | 9/1985 | Remijan | |
| 5,959,711 A | 9/1999 | Silverstein et al. | |
| 6,540,357 B1 | 4/2003 | Ohnuma et al. | |
| 7,997,732 B2 * | 8/2011 | Ramella-Roman et al. | .. 351/213 |
| 2002/0065468 A1 | 5/2002 | Utzinger et al. | |
| 2003/0038921 A1 | 2/2003 | Neal et al. | |
| 2005/0041207 A1 | 2/2005 | Miller et al. | |
| 2005/0057441 A1 | 3/2005 | Park | |
| 2005/0110949 A1 | 5/2005 | Goldfain et al. | |
| 2006/0146284 A1 | 7/2006 | Collins et al. | |
| 2007/0159595 A1 | 7/2007 | Fukuma et al. | |
| 2007/0177004 A1 | 8/2007 | Kolehmainen et al. | |

OTHER PUBLICATIONS

Jacques, S.L., et al., "Polarized Light Imaging of Tissues", Chapter 19, *Lasers and Current Optical Techniques in Biology*, G. Palumbo, R. Pratesi, eds., Comprehensive series in photochemistry and photobiology, vol. 4, publ. The Royal Society of Chemistry, Cambridge, UK, pp. 593-607 (2004).

Nabili, A., et al. "Calibration of an eye oximeter with a dynamic eye phantom" *Proceedings of SPIE*, vol. 6870, pp. 68700N-68700N-10 (2008).

(Continued)

*Primary Examiner* — Ricky Mack
*Assistant Examiner* — Zachary Wilkes
(74) *Attorney, Agent, or Firm* — Vedder Price PC

(57) ABSTRACT

The multi-aperture system of the present invention provides a retinal oximetry apparatus for determining the level of oxygen saturation in retinal vessels using a lenslet array comprising at least seven lenses for the simultaneous measurement of reflected light with at least three wavelengths and at least four polarization states. The multi-aperture system of the present invention further provides an apparatus for determining the level of oxygen saturation in retinal vessels using a lenslet array comprising at least ten lenses for the simultaneous measurement of reflected light with at least three wavelengths for oxygen measurement, at least three wavelengths for melanin content, and at least four polarization states. Methods of operating the same are also provided.

3 Claims, 24 Drawing Sheets

OTHER PUBLICATIONS

Ramella-Roman, Jessica A., et al. "Spectroscopic Measurements of Oxygen Saturation in the Retina", *IEEE Journal of Selected Topics in Quantum Electronics*, vol. 13, No. 6, (Nov./Dec. 2007).

Schweitzer, Dietrich, et al. "Calibration-free measurement of the oxygen saturation in retinal vessels of men", *SPIE*, vol. 2393, pp. 210-218 (May 1995).

Anderson, et al., "The Optics of Human Skin," The Journal of Investigative Dermatology, 77: 13-19, 1981.USA.

Beach, et al., "Oximetry of retinal vessels by dual-wavelength imaging: calibration and influence of pigmentation," 8750-7587/99, 748-757, 1999.

De Kock, et al, "Reflectance Pulse Oximetry Measurements from the Retinal Fundus," IEEE Transactions on Biomedical Engineering, vol. 40, No. 8, Aug. 1993.

Delori, Francois C., "Noninvasive technique for oximetry of blood in retinal vessels," Applied Optics, vol. 27, Mar. 15, 1988, Optical Society of America, 1987. USA.

Delori, et al., "Spectral reflectance of the human ocular fundus," Applied Optics, vol. 28, No. 6, Mar. 15, 1989, Optical Society of America, 1989.

Denninghoff, et al., "Retinal venous oxygen saturation and cardiac output during controlled hemorrhage and resuscitation," J. Appl. Physiol 94: 891-986, 2003, USA.

Denninghoff, et al., "Retinal Large Vessel Oxygen Saturations Correlate with Early Blood Loss and Hypoxia in Anesthetized Swine," The Journal of Trauma: vol. 43, 1997, 29-34.

Drewes, et al., "An Instrument for the Measurement of Retinal Vessel Oxygen Saturation," SPIE, vol. 3591, SPIE Conference on Opthalmic Technologies IX, Jan. 1999, USA.

Faber, et al., "Oxygen Saturation-Dependent Absorption and Scattering of Blood," Physical Review Letters, vol. 93, No. 2, 028102-1-028102-4, Jul. 9, 2004.

Hammer, et al., "Optical properites of ocular fundus tissues an in vitro study using the double-integrating-sphere . . ." Phys. Med. Biol. 40 (1995) 963-978, United Kingdom.

Hammer, et al., "Light Paths in Retinal Vessel Oxymetry," IEE Trans Biomed Eng. 48 (5):592-8 (2001).

Hammer, et al., "Retinal vessel oximetry-calibration, compensation for vessel diameter and fundus pigmentation, and . . . ," J. of Bioned. Opt. 13(5):054015-1-054015-7, 2008.

Harris, et al., "A Review of Methods for Human Retinal Oximetry," Ophthalmic Surg. Laser Imag. 34 (2): 152-164 (2003).

Harvey, et al., "Spectral Imaging in a Snapshot," Spectral Imaging Instrumentation, Applications, and Analysis III, vol. 5694, SPIE, 2005, 1605-7422, USA.

Harvey, et al., "Spectral imaging of the retina," Fourth International Conference on Photonics and Imaging in Biology and Medicine, vol. 6047, 2006.

Hickman, et al., "A Study of Retinal Venous Blood Oxygen Saturation in Human Subjects by Photographic Means," American Heart Association, Circulation 27: 375-385 (1963).

Hickman, et al., "Studies of the Retinal Circulation in Man: Observations on Vessel Diameter, Arteiovenous Oxygen . . . " American Heart Association, Circulation 1966, 33:302-316.

Johnson, et al., "Snapshot hyperspectral imaging in ophthalmology," Journal of Biomedical Optics 12(1), 014036 (Jan.-Feb. 2007).

Kohner, et al., "Role of Blood Flow and Impaired Autoregulation in the Pathogenesis of Diabetic Retinopathy," Diabetes, vol. 44: 603-07, Jun. 1995.

Nelder, et al., "A simplex method for function minimization," Computer, J., 7:308-313 (1965).

Nguyen, et al., "Supplemental Oxygen Improves Diabetic Macular Edema: A Pilot Study," Investigative Ophtalmology & Visual Science, Feb. 2004, vol. 45, No. 2.

Pittman, et al., "A new method for the measurement of percent oxyhemoglobin," Journal of Applied Physiology, vol. 38, No. 2: 315-320 (1975), USA.

Preece, et al., "Monte Carlo modelling of the spectral reflectance of the human eye," Physics of Medicine and Biology, 47:2863-2877 (2002).

Ramella-Roman, Jessica C., et al., "A lenslet-based device for measuring oxygen saturation . . . " IEEE Journal of Seleced Topics in Quantum Electronics, 13 (6) 1697-1703, 2007.

Ramella-Roman, Jessica C., et al., "Measurement of oxygen saturation in the retina with a spectroscopic . . . " Optics Express 16 (9) 6170-6182 (2008).

Sarna, et al., "The Physical Properties of Melanins," in the Pigmentary System, Oxford University Press, 1998, 439-450.

Schweitzer, et al., "A new method for the measurement of oxygen saturation at the human ocular fundus," International Ophtalmology 23: 347-353, 2001, Netherlands.

Schweitzer, et al., "In Vivo Measurement of the Oxygen Saturation of Retinal Vessels in Healthy Volunteers," IEEE Trans. on Biomed. Engineering, vol. 46, No. 12, Dec. 1999.

Smith, et al., "Oxygen Saturation Measurements of Blood in Retinal Vessels During Blood Loss," Journal of Biomedical Optics 3(3), 296-303, Jul. 1998.

Smith, Matthew H., "Optimum wavelength combinations for retinal vessel oximetry," Applied Optics, vol. 38, No. 1, Jan. 1, 1999.

Smith, et al., "Effect of multiple light paths on retinal vessel oximetry," Applied Optics, vol. 39, No. 7, Mar. 1, 2000.

Takatani, et al., "Theoretical Analysis of Diffuse Reflectance from a Two-Layer Tissue Model," IEEE Transactions on Biomedical Engineering, vol. BME-26, No. 12, Dec. 1979.

Wang, et al., "MCML-Monto Carol modeling of light transport in multi-layered tissues," Computer Methods and Programs in Biomedicine 47 (1995) 131-146, Ireland.

Wangsa-Wirawan, et al., "Retinal Oxygen Fundamental and Clinical Aspects," Arch. Ophthalmol, vol. 121, Apr. 2003.

Wo, et al., "Unreliability of blood pressure and heart rate to evaluate cardiac output in emergency resuscitation and critical illness," Crit. Care Med., 21(2) 218-223, 2003.

\* cited by examiner

LENSLET ARRAY FOR RETINAL OXIMETRY

CROSS-REFERENCE TO RELATED APPLICATIONS

This application is a divisional application of U.S. application Ser. No. 12/262,696, filed Oct. 31, 2008, allowed now U.S. Pat. No. 7,997,732, which claims the priority date of co-pending U.S. Prov. App. No. 61/102,947, entitled "Retinal Oximeter," filed Oct. 6, 2008, and the entire disclosure and contents of this provisional application are hereby incorporated by reference.

BACKGROUND

1. Field of the Invention

The present invention relates to an optical device and to methods for simultaneously projecting a plurality of images of light reflected by a retina of a subject onto a detection system for retinal oximetry measurement.

2. Related Art

One important goal of research concerning blood circulation in the retina is the development of techniques that measure suitable parameters for determining the supply and consumption of oxygen. Such parameters may include both the rate of blood flow as well as the degree of oxygen saturation in retinal vessels. While both parameters are theoretically measurable in vivo, due in large part to the complex structure of the eye affecting both the path and absorbance of incident and reflected light, the measurement and determination of oxygen saturation in the retina has proven more difficult than retinal blood flow. A need continues in the art for improved non-invasive methods and devices for the detection and measurement of oxygen saturation and metabolism in the retina.

SUMMARY

According to a first broad aspect of the present invention, a multi-aperture system for retinal oximetry is provided comprising: a lenslet array; a filter array; and a detection system for detecting light passing through said lenslet array and said filter array, wherein said lenslet array comprises at least seven lenses; wherein said filter array comprises at least seven openings, at least three different wavelength filters, and at least two linear polarizers oriented at different angles; and wherein said lenslet array is positioned closer than said filter array to said detection system.

According to a second broad aspect of the present invention, a multi-aperture system for retinal oximetry is provided comprising: a lenslet array; a filter array; and a detection system for detecting light passing through said lenslet array and said filter array, wherein said lenslet array comprises at least ten lenses; wherein said filter array comprises at least ten openings, a first group of at least three different wavelength filters, a second group of at least three different wavelength filters, and at least two linear polarizers oriented at different angles; and wherein said lenslet array is positioned closer than said filter array to said detection system.

According to a third broad aspect of the present invention, a method for retinal oximetry is provided comprising the following steps: (a) placing an eye of a subject at the entrance pupil of an optical device; and (b) detecting a plurality of two-dimensional images of light reflected by the retina of the eye of the subject using the multi-aperture system of claim 1 attached to the exit pupil of the optical device.

BRIEF DESCRIPTION OF THE DRAWINGS

The invention will be described in conjunction with the accompanying drawings, in which.

DETAILED DESCRIPTION OF THE PREFERRED EMBODIMENTS

Definitions

Figure 1A:
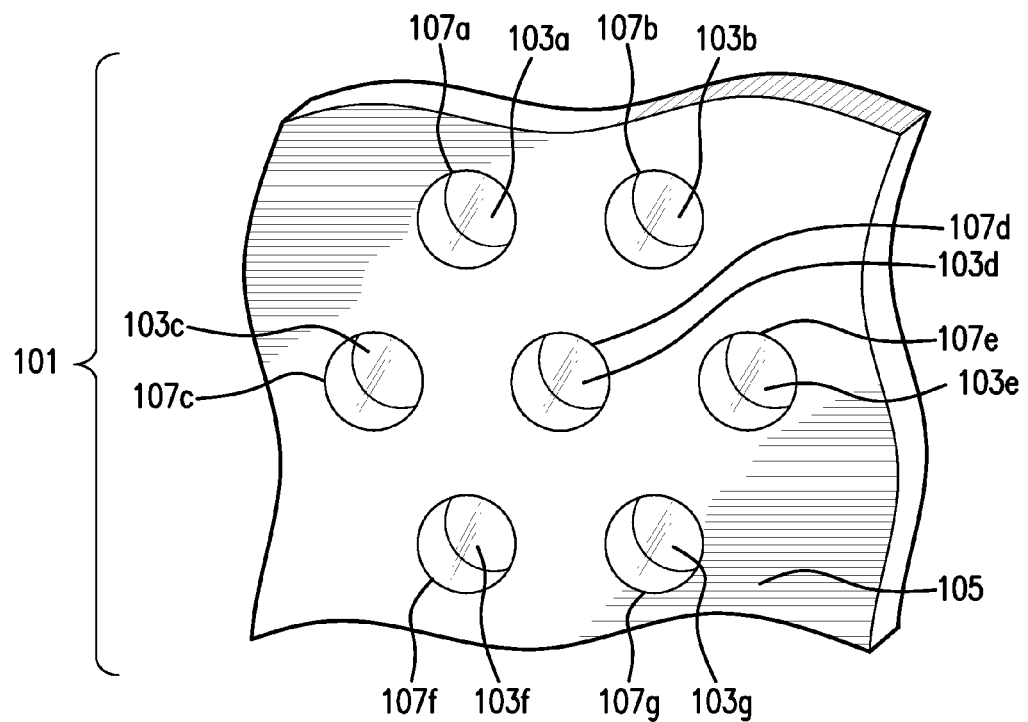
FIG. 1A is a cut-away perspective view of an exemplary lenslet array of a multi-aperture system according to embodiments of the present invention having at least seven (7) lenses.

It is advantageous to define several terms before describing the invention. It should be appreciated that the following definitions are used throughout this application.

For the purposes of the present invention, the terms "subject" or "individual" may refer interchangeably to a person or animal subjected to analysis using a multi-aperture system of the present invention. The "subject" or "individual" allow their eye to be examined to determine the level of oxygen saturation in the retina.

For the purposes of the present invention, the term "incident light" refers to light that enters the pupil of the eye and illuminates the retina of a subject, unless otherwise described.

For the purposes of the present invention, the term "reflected light" generally refers to light that is reflected by a surface, material, tissue, etc. that is analyzed by the multi-aperture system of the present invention, unless otherwise described. For example, such reflected light may refer to light reflected by a reflectance standard or the retina of a subject.

For the purposes of the present invention, the term "optical device" may refer to any device that may be used to view light reflected by the retina of a subject. For example, such optical device may include a fundus opthalmoscope, a slit lamp, etc.

For the purposes of the present invention, the term "entrance pupil" refers to the point of exit for incident light from the optical device and/or to the point of entry for light reflected by the retina of a subject into the optical device.

For the purposes of the present invention, the term "exit pupil" refers to the point of exit for light reflected by the retina of a subject from the optical device.

For the purposes of the present invention, the term "wavelength filter" may refer to a band-pass (or narrow-band) filter, a high-pass filter, or a low-pass filter, or any combination thereof, that may be used to only allow a particular range (or ranges) of light wavelengths to be transmitted. Wavelength filters may be defined in terms of their peak transmission wavelength.

For the purposes of the present invention, the term "peak transmission wavelength" in reference to a wavelength filter refers to the wavelength of light having the maximum or near maximum transmission intensity (i.e., the lowest absorbance and/or reflection) through the wavelength filter.

For the purposes of the present invention, the terms "polarizer," "polarizing material," or "polarization material" may refer interchangeably to a material that allows light polarized at a particular angle to be transmitted to a much greater extent than polarized light oriented at 90° relative to such particular angle.

For the purposes of the present invention, the term "detection system" generally refers to any device that may be used analyze, capture, record, etc. an image and that may be interface with a multi-aperture system of the present invention. For example, such detection system may include film, a CCD, or any other suitable camera device.

For the purposes of the present invention, the term "detection surface" generally refers to a two-dimensional layer, surface, etc. of a detection system that interacts or reacts chemically or physically with light to generate a signal or product that may be used in turn to determine the amount of light striking a given position of such detection surface. For example, in reference to photographic film, the film itself is the detection surface, whereas the array of photoactive sensors of a CCD may be considered the detection surface.

For the purposes of the present invention, the term "upstream" refers to a direction that is away from the detection system and toward the origin of reflected light, such as a reflectance standard or the retina of a subject. For example, the term "upstream" may refer to a direction that is toward an optical device attached to a multi-aperture system of the present invention.

For the purposes of the present invention, the term "downstream" refers to a direction that is toward the detection system and away from the origin of reflected light, such as a reflectance standard or the retina of a subject. For example, the term "downstream" may refer to a direction that is away from an optical device attached to a multi-aperture system of the present invention.

For the purposes of the present invention, the term "solid matrix" may refer to any material that is sufficiently rigid to support and hold the lenses of the lenslet array in place or to support and hold wavelength filters, polarizers, and/or wave plates in place over openings of filter array. Such a "solid matrix" may be made of any metal (e.g., aluminum, etc.), plastic (e.g., Delrin® by Dupont, etc.), or other polymeric material.

For the purposes of the present invention, the term "uncovered" in reference to an opening in a filter array may refer to any opening that is not directly associated with or in close proximity to any wavelength filter, polarizer, and/or wave plate. Generally speaking, light that passes through the "uncovered" opening of the filter array does not pass through any wavelength filter, polarizer, and/or wave plate.

For the purposes of the present invention, the term "covered" in reference to an opening in a filter array may refer to any opening that is directly associated with or in close proximity to any wavelength filter, polarizer, and/or wave plate. Generally speaking, light passing through such "covered" opening of solid matrix of the filter array also passes through a wavelength filter, polarizer, and/or wave plate. An opening of a filter array may be considered "covered" even though a wavelength filter, polarizer, and/or wave plate does not physically contact the solid matrix of the filter array or a wavelength filter, polarizer, and/or wave plate is located within the interior of such opening of the filter array.

For the purposes of the present invention, a wavelength filter, polarizer, and/or wave plate may be considered to "cover" an opening of a filter array is such opening of the filter array is covered by the wavelength filter, polarizer, and/or wave plate. Alternatively, a wavelength filter, polarizer, and/ or wave plate may be considered to "cover" an opening of a filter array if the wavelength filter, polarizer, and/or wave plate spans the cross-section of an opening of the filter array.

For the purposes of the present invention, the term "cross-section" in reference to an opening in the filter array refers to the area of such opening measured in the plane of the filter array.

For the purposes of the present invention, the term "parallel" in reference to the arrangement a lenslet array and a filter array refers to a parallel arrangement of the planes of the lenslet and filter arrays.

For purposes of the present invention, the terms "multi-aperture screen" or "focusing screen" may refer to a screen having multiple apertures to selectively allow light to pass through. The arrangement of apertures of the multi-aperture screen will generally be the same as the arrangement of lenses in the lenslet (or combined) array and/or the arrangement of openings in the filter array.

DESCRIPTION

There is great interest in determining oxygen saturation in the retina vessels. Measurement of blood oxygenation levels in the retina may be used to provide critical insight into early pathologic changes and may be used as an important tool during critical care. See, e.g., Nguyen et al., "Supplemental oxygen improves diabetic macular edema: a pilot study," *Invest. Ophthalmol. Visual Sci.* 45:617-624 (2004); Denninghoff et al., "Retinal large vessel oxygen saturation correlates with early blood loss and hypoxia in anesthetized swine," *J. Trauma.* 43:29-34 (1997); and Denninghoff et al., "Retinal venous oxygen saturation and cardiac output during controlled hemorrhage and resuscitation," *J. Appl. Phys.* 94:891-896 (2003), the entire contents and disclosures of which are hereby incorporated by reference. Noninvasive measurement of oxygen saturation in the retina is desirable for many different clinical applications. For example, early changes in auto-regulation and blood flow in the retina have been linked to the onset of diabetic retinopathy (DR) and vision loss, which significantly decrease in an individual's quality of life. See, e.g., Kohner et al., "Role of blood flow and impaired auto-regulation in the pathogenesis of diabetic retinopathy," *Diabetes* 44:603-607 (1995), the entire contents and disclosure of which are hereby incorporated by reference. Although mechanisms for retinal damage in the late stages of detectable DR have been described, early changes, leading to the onset of disease, are not well understood.

Various studies have suggested that early detection and treatment of diabetic retinopathy and diabetic macular edema may significantly reduce the risk of visual loss. See, e.g., Wangsa-Wirawan et al., "Retinal oxygen: fundamental and clinical aspects," *Arch Ophthalmol.* 121:547-557 (2003), the entire contents and disclosure of which are hereby incorporated by reference. Lack of oxygenation in the retina and any resulting abnormal angiogenesis may lead to loss of retinal tissue and vision impairment. See, e.g., Denninghoff et al., (2003), supra. Indeed, recent studies have shown that macular edema can be reduced by supplementing oxygen to patients. See, e.g., Nguyen et al., (2004), supra. Therefore, it is important to develop minimally invasive tools for the measurement of oxygen saturation in the retina to monitor DR progress.

Oxygen delivery cannot be directly determined from ordinary vital signs. However, the retina provides an ideal site for monitoring blood oxygen levels since retinal vessels are optically accessible and provide a good central perfusion bed that is generally insensitive to shock. Measurement of blood oxygenation in the retina may provide not only insight into early stages of retinal disease, but may also serve as a gateway for the determination of oxygen delivery to other tissues. For example, measurement of oxygen saturation in the retina may be used to determine oxygen delivery to vital organs such as the brain. See, e.g., Smith et al., "Oxygen Saturation measurements of blood in retinal vessels during blood loss," *J. Biomed. Opt.* 3:296-303 (1998), the entire contents and disclosure of which are hereby incorporated by reference. Alternatively, for example, measurement of oxygen saturation in the retina may be used to detect blood loss associated with trauma or other hemorrhaging conditions. See, e.g., Denninghoff et al., (2003), supra.

While venous oxygen saturation is related to local oxygen metabolism, arterial oxygen saturation is generally related to a patient's respiratory function. Differences between arterial and venous oxygen saturation may be used to infer the amount of oxygen consumption or metabolism in a particular location or tissue, such as the retina. Although invasive procedures for monitoring oxygen delivery, such as fiber optic sensors inserted into the heart and pulmonary artery, are available (See, e.g., Wo et al., "Unreliability of blood pressure and heart rate to evaluate cardiac output in emergency resuscitation and critical illness," Crit. Care Med. 21:218-223 (1993), the entire contents and disclosure of which are hereby incorporated by reference) and may be employed in a hospital environment, these techniques are generally not suited for ambulatory or routine medical care and do not provide any direct measurement of oxygen saturation in the retina.

Several groups have worked on instruments, methods, and algorithms targeted at measuring oxygen saturation in the retina. In general, these instruments and methods rely on the Lambert-Beer law and the wavelength-dependent interaction of light with hemoglobin. The Lambert-Beer law holds that light transmitted through a solution diminishes logarithmically as the concentration and thickness of a sample increases relative to the incident light. This expression for any absorbing substance contained in a solution of thickness/at a given wavelength ($\lambda$) may be written as:

$$D(\lambda) = \log(I_o/I) = \epsilon \cdot c \cdot l \quad (1)$$

where $I_o$ is the incident light, I is the transmitted light, c is the concentration, and $\epsilon$ is the specific extinction coefficient at such wavelength. However, in the context of retinal imaging, only reflected (not transmitted) light may be measured. Therefore, the incident light ($I_o$) is often assumed to be light reflected from portions of the retina adjacent to blood vessels with transmitted light (I) traveling or traversing through retinal vessels:

$$D(\lambda) = -\log(I_{vessel}/I_{background}) \quad (2)$$

For a mixture that contains more than one absorbing substances, the Lambert-Beer law may be written as:

$$D(\lambda) = \epsilon_1 \cdot c_1 \cdot l_1 + \epsilon_2 \cdot c_2 \cdot l_2 + \ldots + \epsilon_n \cdot c_n \cdot l_n \quad (3)$$

The critical feature that makes the measurement of oxygenated hemoglobin possible is that oxygenated and deoxygenated hemoglobin absorb light differently in a wavelength-dependent manner. Therefore, an equation could be written as:

$$D(\lambda) = \epsilon_{HbO_2} c_{HbO_2} l + \epsilon_{Hb} c_{Hb} l \quad (4)$$

Oxygen saturation (s) of blood may be defined as the fraction of oxygenated hemoglobin:

$$s = c_{HbO_2}/(c_{Hb} + c_{HbO_2}) = c_{HbO_2}/c_{Hb_{total}} \quad (5)$$

By combining these equations, new formulas may be derived to express oxygen saturation in terms of optical density. By using multiple equations for different wavelengths of light, various unknowns may be taken into account and determined. Although not essential, these formulas may be simplified by measuring optical density at isosbestic wavelengths (defined as having about equal extinction coefficient values for oxygenated and deoxygenated hemoglobin). In the simplest example, two equations for two wavelengths of light may be used to eliminate variables for total concentration of hemoglobin ($c_{Hb_{total}}$) and thickness (l) to solve for oxygen saturation in terms of observed optical densities at each wavelength $D(\lambda)$. Unfortunately, such a simplistic measurement for oxygen saturation in the retina has proven insufficient in terms of accuracy because of the need to take into account the complex structure of the eye when measuring light reflected from the retina. Indeed, the layered structure of the eye, its many absorbing and scattering components, and its constant movement make this measurement particularly difficult. Therefore, to more accurately determine the level of oxygen saturation in retinal vessels, more variables, and hence more measurements, must be taken into account. For further discussion of basic principles and equations relating to retinal oximetry that may be used with embodiments of the present invention, see, e.g., Harris et al., "A Review of Methods for Human Retinal Oximetry," Ophthalmic Surg. Laser Imag. 34(2):152-164 (2003); and Smith, "Optimum wavelength combinations for retinal vessel oximetry," Applied Optics 38(1):258-267 (1999), the entire contents and disclosures of which are hereby incorporated by reference.

The first retinal oximeter was proposed by Hickam et al. See, Hickam et al., "A study of retinal venous blood oxygen saturation in human subjects by photographic means," Circulation 27:375-385 (1963), the contents and disclosure of which are hereby incorporated in its entirety. Using a modified fundus camera, Hickam et al. imaged the retina on film at two different wavelengths and made calculations of oxygen saturation in vessels using the simplest Lambert-Beer law approach described above. In 1975, Pittman and Dulling showed that more accurate results of retinal oximetry could be achieved using three wavelengths instead of two by taking onto account a wavelength-dependent scattering coefficient in their model. See, e.g., Pittman et al., "A new method for the measurement of percent hemoglobin," J. Appl. Phys. 38:315-320 (1975), the contents and disclosure of which are hereby incorporated in its entirety. However, their approach was based on transmitted light. In 1988, Delori used the three wavelength approach to calculate oxygen saturation by reflection using narrowly spaced wavelengths (558 nm, 569 nm, and 586 nm) to allow a scattering coefficient to be considered constant. See, Delori, F. C., "Noninvasive technique for oximetry of blood in retina vessels," Appl. Opt. 27:1113-1125 (1988), the contents and disclosure of which are hereby incorporated in its entirety. The wavelengths were chosen to maintain high vessel to background contrast and to reduce the impact of light scattering in the ocular media and vessel walls.

Schweitzer et al. designed a point measurement retinal oximeter that could image the retina spectroscopically using light source wavelengths from 400 nm to 700 nm in 2 nm intervals with an empirical scattering model used in their calculations. See, e.g., Schweitzer et al., "Calibration-free measurement of the oxygen saturation in retinal vessel of men," Proc. SPIE 2393:210-218 (1995); Schweitzer et al., "In Vivo Measurement of the Oxygen Saturation of Retinal Vessels in Healthy Volunteers," IEEE Trans. on Biomed. Eng. 46(12):1454-1465 (1999); and Schweitzer et al., "A new method for the measurement of oxygen saturation at the human ocular fundus," Int Ophthalmol. 23:347-353 (2001), the entire contents and disclosures of which are hereby incorporated by reference. Denninghoff et al. used two diode lasers at 670 nm and 830 nm in their eye oximeter (EOX) to scan across a retinal vessel and calculate oxygen content. See, e.g., Denninghoff et al., (1997), supra; Smith et al., "Oxygen Saturation Measurements of Blood in Retinal Vessels during Blood Loss," J. of Biomedical Optics 3(3):296-303 (1998); Smith et al., "Effect of multiple light paths on retinal vessel oximetry," Applied Optics 39(7):1183-1193 (2000); and Denninghoff et al., (2003), supra, the entire contents and disclosures of which are hereby incorporated by reference. Similarly, Drewes et al. used four different lasers in a confocal system (629, 679, 821, and 899 nm) to obtain one-dimensional absorption curves. See, Drewes et al., "An instrument for the measurement of retinal vessel oxygen saturation," Proc. SPIE 3591:114-120 (1999), the contents and disclosure of which is hereby incorporated by reference in its entirety.

Finally, Johnson et al. have used a hyper-spectral imager to obtain 50 retina images between 450 and 700 nm using a diffractive grating with oxygen saturation obtained via a Monte Carlo based method. See, Johnson et al., "Snapshot hyper-spectral imaging in ophthalmology," *J. Biomed. Opt.* 12:14036-14043 (2007), the entire contents and disclosure of which are hereby incorporated by reference.

Although these approaches have gradually improved the accuracy for determining oxygen saturation in the retina, these devices and methods remain imperfect and suffer from a number of limitations. For example, the approach in Hickam et al. used alternating filters to capture each retinal image sequentially. However, because the apparatus in Hickam et al. must make each measurement sequentially, a great amount of time and operation would be required to obtain separate optical measurements. There would also be difficulty in accurately accounting for eye movement and changing conditions over the course of an examination. Tiedeman et al. used image-splitting optical instruments and filters to create two simultaneous retinal images. See, e.g., Beach et al., "Oximetry of retinal vessels by dual-wavelength imaging: calibration and influence of pigmentation," *J. Appl Physiol* 86:748-758 (1999), the entire contents and disclosure of which are hereby incorporated by reference. However, any apparatus relying on beam splitters and other optical elements, such as in Tiedeman et al., is physically limited by the difficulty in constructing complex optical instruments that are capable of splitting light into greater than 2 or 3 light paths for separate and simultaneous filtering and measurement. As described above, a greater number of wavelength measurements are needed to accurately determine oxygen saturation.

Schweitzer et al. illuminated a slit-like field of the retinal fundus to create a one-dimensional field of reflected light spanning a retinal vessel. This one-dimensional field of light was then confocally imaged by scanning across the one-dimensional field with light reflected from each point of the scan separated into a spectrum of component wavelengths in a second dimension via a spectrographic grating. This data was then used to create an imaging reflecting spectrum plot across the scanned one-dimensional imaging field. One problem with the approach in Schweitzer et al. is that it is very sensitive to eye movement over the course of the scan. While image tracking software may be used to realign the data, there may be difficulty with calibration since the exact position and origin of the light may be uncertain. Furthermore, the approach in Schweitzer et al. is limited by only imaging a short one-dimensional field spanning a vessel. More recent attempts by Schweitzer et al. have sought to apply their empirical knowledge gained from their spectrographic approaches to a more limited set of discrete wavelength-dependent images. See, e.g., Hammer et al., "Retinal vessel oximetry-calibration, compensation for vessel diameter and fundus pigmentation, and reproducibility," *J. of Biomed. Optics* 13(5):054015-1-054015-7 (2008), the contents and disclosure of which is hereby incorporated by reference in its entirety.

Denninghoff et al. used a series of monochromatic lasers to scan one-dimensionally across a selected retinal vessel. However, similarly to Schweitzer et al., this approach is sensitive to eye movements that occur over the course of the scans and only provides information for a short one-dimensional segment of the retina. In addition, the EOX approach of Denninghoff et al. relies on the use of expensive laser equipment that may not be readily interfaced with standard fundus opthalmoscopes.

Therefore, each of these methods and approaches to retinal oximetry is limited in a number of ways: (1) by the number of simultaneous two-dimensional images at different wavelengths that may be acquired, (2) the small one-dimensional cross-section that may be measured during a single scan, (3) the sensitivity of measurements to eye movements, and/or (4) the use of expensive or non-compatible equipment. Furthermore, none of these devices could be used to simultaneously acquire meaningful polarization and spectroscopic information from whole images generated from light reflected by the retina of an individual. Although Johnson et al. (See, e.g., Johnson et al., (2007), supra) has developed a computed tomographic imaging spectrometer (CTIS) that is capable of capturing both spatial and spectral information in a single frame, this approach is unable to simultaneously generate wavelength- and polarization-dependent images.

One of the major issues hindering accurate determination of oxygen saturation in the retina by various retinal oximetry approaches is light scattered or specularly reflected by the surfaces and interfaces of cells, vessels, and other particles, which complicate the wavelength-dependent interpretation of light reflected by the fundus. Light that is specularly reflected will not have traversed all of the layers of the retina and, therefore, may provide no information about the contents of the retina. Furthermore, scattered light may lose its positional signature and may even be deflected away from detection altogether giving the anomaly of having been absorbed. As described above, several attempts have been made to better model these variables in mathematical terms by increasingly complex formulas and by making a greater number of wavelength measurements.

Polarization status provides another tool in addition to wavelength information for assessing the characteristics of light reflected by the retinal fundus. By linearly polarizing incident light on the retina in a predetermined orientation, light reflected from the retina may be characterized according to its polarization state (i.e., whether reflected light conforms or deviates from the polarization state of incident light). Light that is specularly reflected or scattered by the surface or interface of retinal structures, such as a vessel or red blood cell, may be expected to have certain properties. For example, specularly reflected light may be expected to have the same or similar polarization state as the incident light, whereas light having an altered polarization state may be more likely to have interacted with structures and contents of the retina, such as hemoglobin. Once this polarization information is known, the contribution of unaltered reflected light to total reflected light may be eliminated to isolate light having altered polarization for the oxygen saturation analysis.

The polarization state of light may also be used to determine the locations of structural components of the retina. For example, light having a particular polarization state may indicate that such light interacted with a specific component of the retina, such as melanin. On the basis of such information, the distribution and prevalence of such components of the retina may be determined. For example, light interacting with a particular component of the retina, such as melanin, may emerge with a specific polarization state, which may have a different polarization state than incident light. This information may be used in turn to determine the distribution and prevalence of such components in the retina and to potentially adjust for the expected absorbance and/or scattering effects of such components on reflected light. According to embodiments of the present invention, this information may be used to provide improved non-invasive methods and devices for the detection and measurement of oxygen saturation and metabolism in the retina.

According to embodiments of the present invention, one way to characterize the polarization state of light is according to the Stokes vector defined by Stokes parameters. The Stokes vector and associated parameters are known in the art. The Stokes vector may be determined by shining linearly polarized light onto the retina and making four separate measurements of the reflected light using different polarizers and/or wave plates: (1) no polarization material, (2) linear polarization material at 45° relative to the polarization of incident light, (3) linear polarization material at 90° relative to the polarization of incident light, and (4) a quarter-wave plate followed by a linear polarization material at 45° relative to the polarization of incident light. By comparing linearly polarized light emerging from the 45° polarizer or the 90° polarizer to light that does not pass through any polarization material after reflection, the linear polarization state of light reflected by the fundus may be determined. In addition, by comparing light emerging from the coupled quarter-wave plate and linear polarizer to light that does not pass through any polarization material after reflection, the circular polarization state of light reflected by the fundus may be determined. For further discussion, see, e.g., Jacques, S. L. and Ramella-Roman, J. C., "Polarized light imaging of tissue." In: *Laser and current optical techniques in biology, Comprehensive series in Photo-Sciences*, Giuseppe Palumbo and Riccardo Pratesi (Eds.), ESP book series (2005), the entire contents and disclosure of which are hereby incorporated by reference.

Embodiments of the present invention seek to implement an optical multi-aperture system that is capable of simultaneously generating a plurality of separate wavelength- and polarization-dependent images in a single snapshot with each image corresponding to approximately the same two-dimensional space of the retina of an individual. This objective is generally achieved using a plurality of lenses arranged in a lenslet array with a corresponding arrangement of wavelength filters, wave-plates, and/or linear polarization materials in a filter array.

Unlike prior devices, embodiments of the present invention are capable of simultaneously generating a large number of wavelength- and polarization-dependent images in a single snapshot corresponding generally to the same two-dimensional area of the retina of an individual or subject. None of the previously described retinal oximeters provide an apparatus or method that is capable of simultaneously generating a plurality of two-dimensional images of light reflected by the retina in a single snapshot, wherein a subset of such images are passed through a plurality of selected wavelength filters and another subset of images are separately passed through a plurality of selected polarization materials. Instead, prior devices and methods are limited to either a small number (i.e., two or three) of simultaneous two-dimensional images, or a limited time-course of one-dimensional scans using devices that are not capable of simultaneously generating polarization images in a practical way. One exception, Johnson et al., (2007), supra, is capable of generating a large amount of wavelength-dependent information for a two-dimensional image of the retina. However, the approach in Johnson et al. could not be used to simultaneously generate both wavelength- and polarization-dependent images from light reflected by the retina of a subject in a single snapshot.

Unlike any of the prior apparatuses and methods, embodiments of the present invention provide an apparatus and method for the simultaneous generation of a plurality of wavelength- and polarization-dependent images of light reflected by the retina of a subject in a single snapshot to provide greater amount of information that may be used to more accurately determine oxygen saturation within a two-dimensional area of the retina. According to embodiments of the present invention, an apparatus is provided that is capable of simultaneously projecting a plurality of two-dimensional images onto a detection system in a single snapshot with each two-dimensional image corresponding to light reflected from approximately the same spatial coordinates of the retina of a subject.

According to some embodiments, for example, a multi-aperture system or apparatus may be capable of generating at least seven (7) two-dimensional images of reflected light corresponding to approximately the same spatial coordinates of the retina of a subject. For example, such apparatus or system may comprise at least three (3) images produced by filtering the light through three different wavelength-dependent filters and at least four (4) different images produced by linear polarizers and/or wave plates (or in the absence of polarizers or wave plates—i.e., no polarizers or wave plates). The linear polarizers may include linear polarization materials oriented at 45° and at 90° relative to the linear polarization angle of incident light and may be used to determine the linear polarization state of reflected light. The quarter-wave plate followed by linear polarizer at 45° relative to the polarization angle of incident light may be used to determine the circular polarization state of reflected light. According to some embodiments, one of the at least four two-dimensional images for polarization may not pass through any polarization material or wave plate, which may be used as a basis for comparing the other polarization-dependent image measurements. As described above, four polarization-dependent measurements may generally be used since this is the number of measurements needed to determine all of the Stokes parameters to completely characterize the polarization state of light, and at least three wavelength-dependent measurements are generally made since this is the minimum number needed to measure oxygen saturation while accounting for light scattering.

According to other embodiments, for example, a multi-aperture system or apparatus may be capable of generating at least ten (10) two-dimensional images of reflected light corresponding to approximately the same spatial coordinates of the retina of a subject. For example, such apparatus or system may comprise at least six (6) images produced by six different wavelength-dependent filters and four (4) different images produced by polarization filters and/or no filter. In addition to making at least three different wavelength-dependent images for measuring oxygen saturation and at least four polarization-dependent images, at least three different and distinct wavelength-dependent images may be used, for example, to measure the melanin content in the retina.

FIG. 1A shows a cut-away drawing of a lenslet array 101 of a multi-aperture system according to embodiments of the present invention having at least seven lenses 103(a-g). Lenses 103(a-g) are generally arranged in a single plane and held in place by a solid matrix 105. Each of the lenses 103(a-g) of the lenslet array 101 may be held in place by the solid matrix 105 by inserting lenses in direct contact with slots 107(a-g) of solid matrix 105.

FIG. 1A shows a minimum number of lenses in the solid matrix of the lenslet array. However, the number of lenses may be much greater, and the size of the solid matrix may vary depending on the circumstances. The solid matrix may be made of any suitable material that is sufficiently rigid to hold the lenses in a fixed position in relation to one another, such as, for example, a plate made of metal, plastic, or other polymeric materials.

The lenses 103(a-g) of lenslet array 101 are shown in FIG. 1A in a 2:3:2 arrangement. However, lenses may have any arrangement and relative spacing in the lenslet array that would be appropriate. However, lenses may be arranged in the lenslet array to maximize usage of the detection surface (not shown) of a detection system (i.e., to minimize the amount of unused or wasted space on the detection surface of a detection system) used for visualization or detection of a plurality of retinal images projected by the lenslet array of a multi-aperture system of the present invention. Each column and/or row of lenses in the lenslet array may be positioned to fit a greater number of lenses within a given area of the solid matrix. Lenses in one row or column may be positioned approximately on a midline between two lenses of an adjacent row or column. For example, lens 103d is shown in FIG. 1A positioned approximately on a midline between lenses of an adjacent row or column (e.g., between 103a and 103b; or between 103a and 103f). The exact spacing between adjacent lenses may vary as long as the plurality of lenses of a multi-aperture system of the present invention allows for most or all of the plurality of retinal images to be projected onto the detection surface of a detection system. For example, the spacing between lenses (measured center-to-center) may be from about 6 mm to about 10 mm. However, some overlap of two-dimensional images projected by the lenslet array of a multi-aperture system on the detection surface of a detection system may be tolerated.

According to embodiments of the present invention, a variety of lens types known in the art may be used in the lenslet array to focus the retinal images onto the surface of a detection system. For example, doublet lenses, such as the Sunex DSL829 (Sunex; Carlsbad, Calif.), may be used. The sizes of the lenses may vary depending on the circumstances. However, typical sizes for lenses may be about 2 mm in diameter. Although FIG. 1A shows each of the lenses of the lenslet array held in place by the solid matrix by inserting lenses in direct contact with slots of solid matrix, one or more lenses of the lenslet array may instead be supported by an additional piece (e.g., a plastic ring) of larger diameter (not shown) that may in turn be directly attached or mounted inside slots of the solid matrix of the lenslet array. The total combined diameter of each lens held by an additional support piece (not shown) may vary. For example, the total combined diameter may be about 6 mm or greater. The size of the slots in the solid matrix of the lenslet array may vary to accommodate (i.e., securely hold) each of the lenses or each of the lenses combined with additional support pieces (not shown).

Figure 1B:
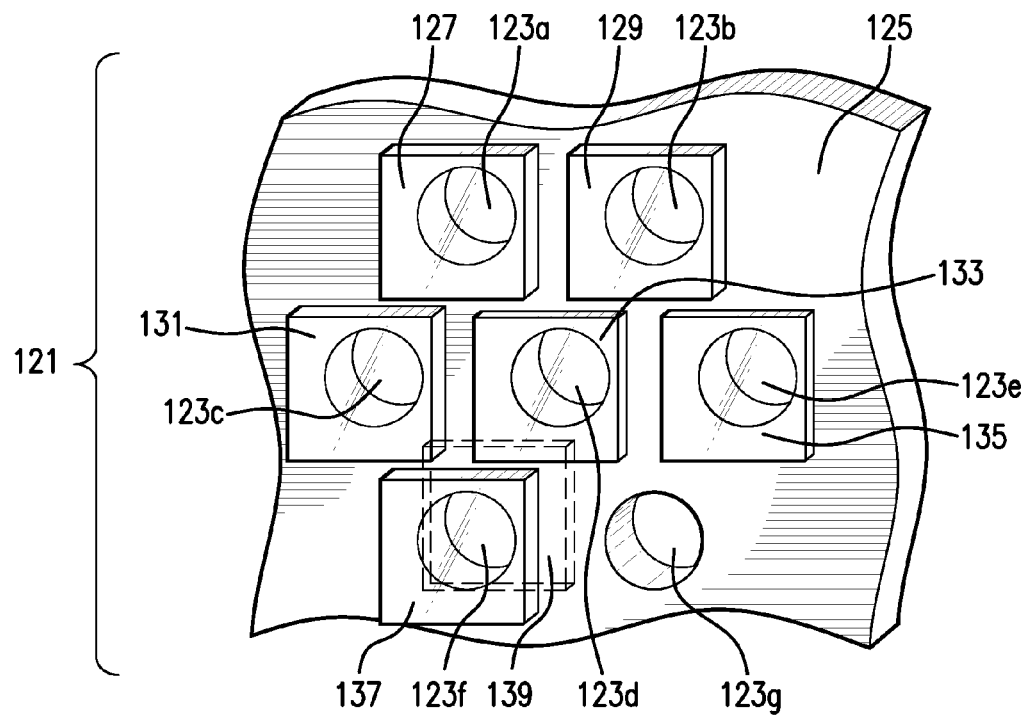
FIG. 1B is a cut-away perspective view of an exemplary filter array of a multi-aperture system according to embodiments of the present invention with openings of filter array separately covered by (i) at least three wavelength filters, (ii) at least two linear polarization filters, (iii) at least one combination of a wave plate and a linear polarizer, and (iv) at least one opening that is uncovered (i.e., no polarizer, filter, or wave plate).

As shown in FIG. 1B, embodiments of the present invention may comprise a filter array 121 of a multi-aperture system having at least seven openings 123(*a-g*) in the solid matrix 125 to allow light to pass through and reach lenses of a lenslet array when filter array and lenslet array are juxtaposed and aligned (see below). To allow light passing through each opening of a filter array of a multi-aperture system to also pass through a corresponding lens of a lenslet array of the multi-aperture system, the openings in the solid matrix of the filter array should be spatially arranged to correspond to the positioning and/or arrangement of lenses in solid matrix of lenslet array. This will allow sufficient light reflected by the retina of a subject to pass through each of the at least seven openings of the filter array, pass through most or all of the diameter of a corresponding lens of the lenslet array, and become projected into a plurality of two-dimensional images onto the detection surface of a detection system. For example, the at least seven lenses 103(*a-g*) of lenslet array 101 are shown in a similar arrangement as openings 123(*a-g*) of filter array 121. When the filter array and the lenslet array are juxtaposed and aligned, light passing through all of the pairs of openings in the filter array and lenses of the lenslet array will create a plurality of two-dimensional images corresponding to light reflected by roughly the same area of the retina of a subject. For example, by juxtaposing filter array 121 and lenslet array 101 shown in FIGS. 1A and 1B, at least seven two-dimensional images may be generated, which correspond to light reflected from roughly the same area of the retina of a subject. By generating a plurality of images that correspond to the same physical coordinates of the retina of a subject, each image may be separately analyzed to determine different components and characteristics of light reflected by the same location of the retina of a subject.

According to embodiments of the present invention, to separately analyze different properties of each image generated by the multi-aperture system, different wavelength filters, polarizers, and/or wave plates may be used to cover different openings of the filter array. At least three different wavelength filters may be used with filter array of a multi-aperture system. Such wavelength filters may include single band-pass filters that allow light having a narrow band of wavelengths with a peak transmission at a particular wavelength(s). Such wavelength filters may include a predetermined set of band-pass filters with each wavelength filter allowing transmission of only wavelengths of light that are relevant to measuring oxygen saturation, which may then be focused by the lenses of the lenslet array of a multi-aperture system onto the detection surface of a detection system. As shown in FIG. 1B, different wavelength filters (127, 129, or 131), polarizers (133, 135, or 139), and/or waveplates 137 may be associated with filter array 121.

According to embodiments of the present invention, although the peak transmission wavelengths of the wavelength filters may potentially be anywhere between about 400 nm and about 700 nm, wavelengths between about 500 nm and about 600 nm are generally preferred for use in directly calculating oxygen saturation in a retinal vessel. For example, the at least three different wavelength filters may be selected from those having the following approximate peak transmission wavelengths: 450, 460, 480, 500, 505, 515, 520, 522, 530, 540, 548, 560, 565, 569, 575, 576, 577, 580, 586, 590, 600, 610, 620, 630, 640, 650, 660, and 680 nm. Examples of wavelength filters that may be used are known in the art.

The size and shape dimensions of each wavelength filter need not be precise. The dimensions of a wavelength filter associated with an opening of the filter array only need to be large enough such that most or all of the light passing through such opening of the filter array and its corresponding (aligned) lens of the lenslet array passes through such wavelength filter. However, the dimensions of each wavelength filter may be limited such that each wavelength filter does not interfere with light passing through two or more openings of the filter array. For example, the dimensions of each wavelength filter may be as small as about 2.5 mm×2.5 mm, or larger (e.g., 5 mm×5 mm). Indeed, the wavelength filters may be smaller in dimension than the diameters of the slots of the lenslet array and/or the openings of the filter array in part because each of the lenses of the lenslet array may be smaller than the slots of the lenslet array (e.g., when lenses are held in place by an additional support piece as described above).

In addition to three or more wavelength filters of the filter array, at least two of the openings of a filter array may be used for determining the linear polarization state of light reflected by the retina of a subject. Alternatively, at least four of the openings of a filter array may be used for determining both the linear and circular polarization state of light reflected by the retina of a subject. As shown in FIG. 1B, a first linear polarizer 133 (oriented at 45° relative to a predetermined angle of the linear polarization of incident light) may be placed over one of the openings 123d of the filter array 121, and a second linear polarizer 135 (oriented at 90° relative to a predetermined angle of the linear polarization of incident light) may be placed over another one of the openings 123e of the filter array 121. Furthermore, a quarter-wave plate 137 may be placed over another opening 123f of the filter array 121 associated with a third linear polarizer 139 (oriented at 45° relative to a predetermined angle of the linear polarization of incident light) that may be placed on the opposing side of opening 123f in the solid matrix 125 of filter array 121 as shown. Materials that may be used for linear polarizers and wave plates are known in the art.

One of the openings of a filter array may be left uncovered such that light traveling through such opening will not pass through any wavelength filters, polarizers, and/or waveplates. For example, FIG. 1B shows an opening 123g in solid matrix 125 of filter array 121 as being uncovered. Such unfiltered and unaltered light passing through the uncovered opening may be used as a basis for comparing the polarization state of light passing through other openings of the filter array, such as those openings covered by (i) a first linear polarizer at 45°, (ii) a second linear polarizer at 90°, or (iii) a wave plate in association with a linear polarizer. This information may be used to determine the Stokes parameters and vector. For example as shown in FIG. 1B, unaltered light passing through opening 123g may be used as a basis of comparison for light passing through (i) a first linear polarizer 133 covering opening 123d of filter array 121 at one angle, (ii) a second linear polarizer 135 covering opening 123e of filter array 121, and (iii) a wave plate 137 and an associated third linear polarizer 139 covering opening 123f of filter array 121. As an alternative to leaving at least one of the openings of the filter array uncovered, at least one of the openings of the filter array may instead be covered with a neutral density filter (not shown).

Alternatively, according to some embodiments, a fourth linear polarizer (not shown) oriented at 0° relative to the linear polarization state of incident light associated with an opening of a filter array of a multi-aperture system may be used in place of (or in addition to) an uncovered opening in the filter array. Similarly to the unaltered image generated by passing reflected light through the uncovered opening, images created by reflected light passing through the linear polarizer at 0° may also be used as a basis of comparison for light passing through the first and second linear polarizers oriented at 45° and 90° relative to the polarization state of incident light. This information may again be used to determine the Stokes parameters and vector.

The first and second linear polarizers of the filter array may be used to determine the linear polarization state of light reflected by the retina of a subject, whereas the combination of a quarter-wave plate and its associated third linear polarizer may be used to determine the circular polarization of light reflected by the retina of a subject. The quarter-wave plate may be used to convert circularly polarized light into linearly polarized light, which may then be analyzed with an associated linear polarizer oriented at 45° relative to light incident on the retina. Such information may be used to determine the Stokes vector and parameters as provided above as a way of characterizing the polarization state of light reflected by the retina of a subject. This information may be used, in turn, to account for the unique structural components of the retina of a subject when calculating oxygen saturation.

Similar to wavelength filters, the size and shape dimensions of each polarizer and/or wave plate need not be precise. The dimensions of such polarizers and/or wave plate associated with an opening of the filter array only need to be large enough such that most or all of the light passing through such opening of the filter array and its corresponding (aligned) lens of the lenslet array passes through such polarizer and/or wave plate. However, the dimensions of each polarizer and/or wave plate may be limited such that each polarizer or wave plate does not interfere with light passing through two or more openings of filter array. Indeed, each polarizer and/or wave plate may be smaller in dimension than the diameters of the slots of the lenslet array and/or the openings of the filter array in part because each of the lenses of the lenslet array may be smaller than the slots of the lenslet array (e.g., when lenses are held in place by an additional support piece as described above).

As shown by examples in FIGS. 1C through 1F, filter array and lenslet array of a multi-aperture system according to embodiments of the present invention may be juxtaposed with wavelength filters, linear polarizers, and/or wave plates arranged in a variety ways. In general, filter array is placed "upstream" of lenslet array (i.e., filter array is placed closer to the optical device and eye of a subject (not shown) while lenslet array is placed closer to the detection system). In FIGS. 1C through 1F, light reflected by the retina of a subject generally approaches from the left of each figure, passes through the wavelength filters (e.g., 127, 129, or 131) and linear polarizers (e.g., 133 or 135) of filter array 121, and is then projected by lenses 103 of lenslet array 101 onto a detection system located to the right of each figure.

In each of the examples in FIGS. 1C through 1F, filter array 121 and lenslet array 101 may be positioned such that each of the wavelength filters (e.g., 127, 129, or 131) and/or linear polarizers (e.g., 133 or 135) of filter array 121 may be positioned immediately adjacent to lenses 103 of lenslet array 101 (e.g., less than 1 mm separation) as long as each of the wavelength filters and/or linear polarizers of filter array do not directly contact any of the lenses of the lenslet array. This would apply to other potential embodiments not shown in FIG. 1C through 1F.

Figure 1C:
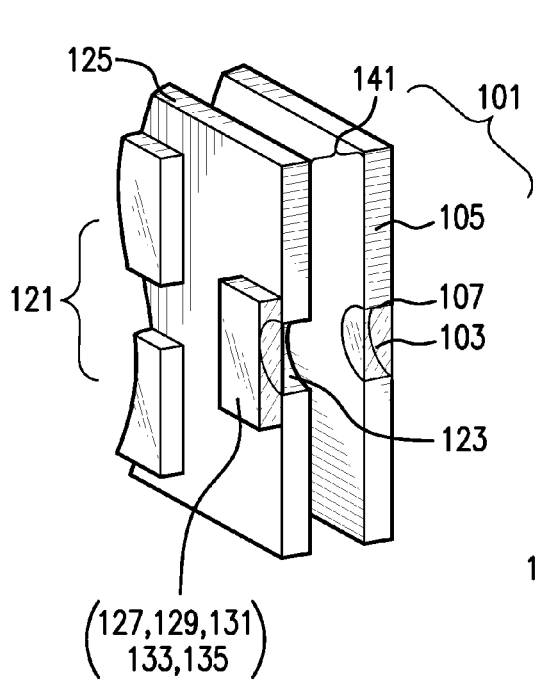
FIG. 1C is a perspective view of a portion of a multi-aperture system showing a portion of a filter array and a portion of a lenslet array juxtaposed according to embodiments of the present invention with a filter/polarizer located on the upstream side of the solid matrix of the filter array.

According to some embodiments, FIG. 1C shows an exemplary arrangement of filter array 121 and lenslet array 101 juxtaposed with wavelength filter (e.g., 127, 129, or 131) or polarizer (e.g., 133 or 135) covering the upstream side of one opening 123 of filter array 121. The filter array 121 and lenslet array 101 is shown in FIG. 1C as being separated by a distance 141. Such distance 141 may be very small. In fact, solid matrices (105 and 125) of filter array 121 and lenslet array 101 may contact one another in this example as long as each wavelength filter (e.g., 127, 129, or 131) or polarizer (e.g., 133 or 135) of the filter array 121 does not physically contact any of the lenses 103 of the lenslet array 101.

Figure 1D:
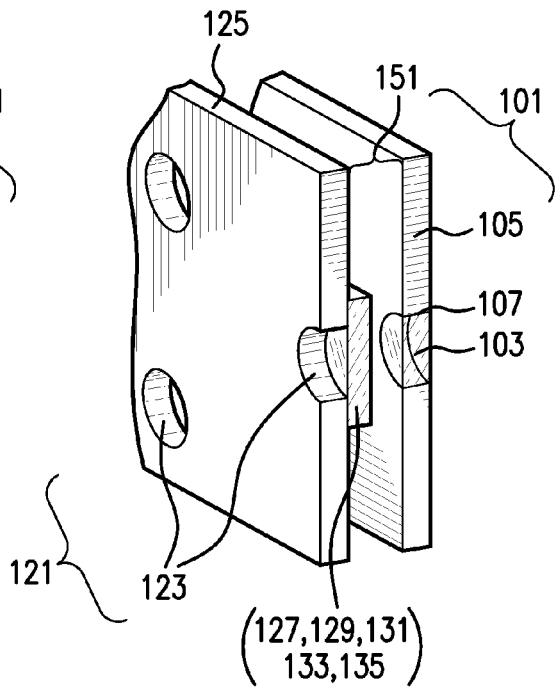
FIG. 1D is a perspective view of a portion of a multi-aperture system showing a portion of a filter array and a portion of a lenslet array juxtaposed according to embodiments of the present invention with a filter/polarizer located on the downstream side of the solid matrix of the filter array.

According to some embodiments, FIG. 1D shows an exemplary arrangement of filter array 121 and lenslet array 101 juxtaposed with wavelength filter (e.g., 127, 129, or 131) or polarizer (e.g., 133 or 135) covering the downstream side of opening 123 of filter array 121. The filter array 121 and lenslet array 101 is shown in FIG. 1D as being separated by a distance 151. In this particular example, solid matrices (105 and 125) of filter array 121 and lenslet array 101 generally may not contact one another since wavelength filter (e.g., 127, 129, or 131) or polarizer (e.g., 133, 135) of filter array 121 is placed between solid matrices (105 and 125) of filter array 121 and lenslet array 101 since this would likely cause wavelength filter (e.g., 127, 129, or 131) or polarizer (e.g., 133, 135) of the filter array 121 to contact a lens 103 of the lenslet array 101. Each wavelength filter (e.g., 127, 129, or 131) or polarizer (e.g., 133, 135) of the filter array 121 may be placed immediately adjacent to solid matrix 105 of lenslet array as long as each wavelength filter (e.g., 127, 129, or 131) or polarizer (e.g., 133, 135) of filter array 121 does not physically contact a lens 103 of the lenslet array 101. However, wavelength filter (e.g., 127, 129, or 131) or polarizer (e.g., 133 or 135) of filter array 121 may contact solid matrix 105 of lenslet array 101 (i.e., distance 151 may become the width of the wavelength filter (e.g., 127, 129, or 131) or polarizer (e.g., 133 or 135)) if, for example, lens 103 is recessed in slot 107 of solid matrix 105 such that direct contact is avoided.

Figure 1E:
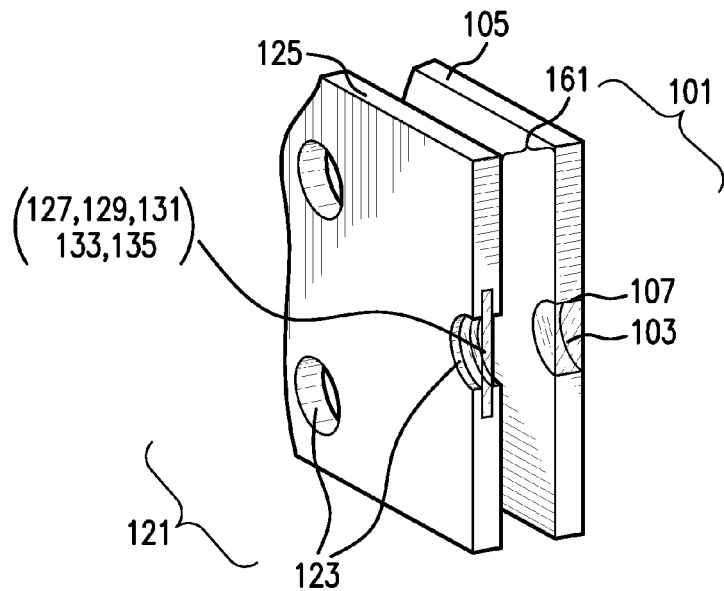
FIG. 1E is a perspective view of a portion of a multi-aperture system showing a portion of a filter array and a portion of a lenslet array juxtaposed according to embodiments of the present invention with a filter/polarizer located inside the solid matrix of the filter array.

According to some embodiments, FIG. 1E provides another example showing an arrangement of filter array 121 and lenslet array 101 juxtaposed with wavelength filter (e.g., 127, 129, or 131) or polarizer (e.g., 133 or 135) inserted within solid matrix 125 of filter array 121. Consistent with this example, solid matrix 125 may comprise two or more pieces of material molded or adhered together to allow wavelength filter (e.g., 127, 129, or 131) or polarizer (e.g., 133 or 135) to be sandwiched and held place. Because wavelength filter (e.g., 127, 129, or 131) or polarizer (e.g., 133 or 135) is held internally within matrix 125 of filter array 121, wavelength filter (e.g., 127, 129, or 131) or polarizer (e.g., 133 or 135) should not be able to contact lenses 103(a-e) of lenslet array 101 even if distance 161 of separation between filter array 121 and lenslet array 101 is negligible or zero.

Figure 1F:
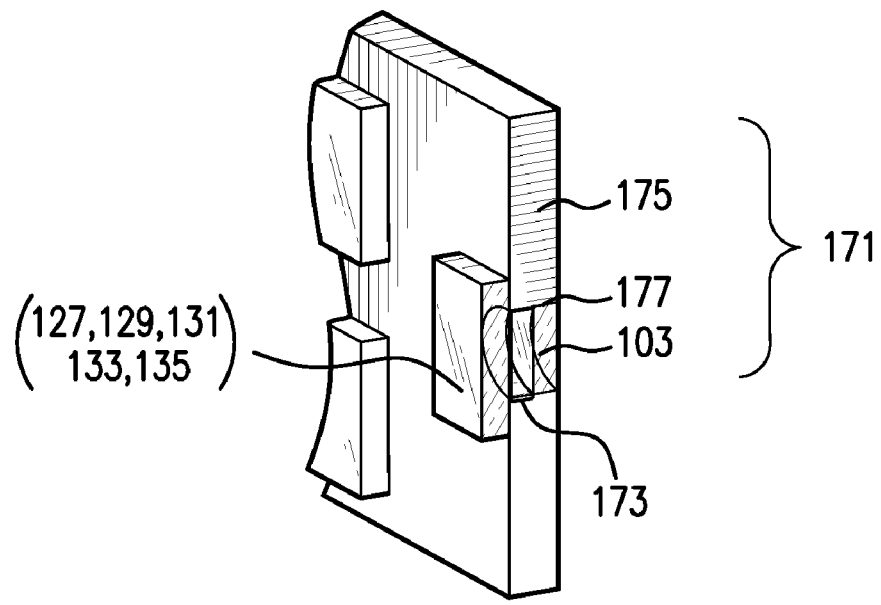
FIG. 1F is a perspective view of a portion of a multi-aperture system showing a combined array of lenses and filters/polarizers held in place by the same solid matrix.

According to some embodiments, FIG. 1F provides yet another example showing a combined array 171 comprising a unified solid matrix 175. Each wavelength filter (e.g., 127, 129, or 131) or polarizer (e.g., 133 or 135) may be placed, for example, overlying the upstream side of each slot 177 of solid matrix 175 of combined array 171. The only requirement is that each wavelength filter (e.g., 127, 129, or 131) or polarizer (e.g., 133 or 135) be separated by a minimal distance 173 from lenses 103 (i.e., each wavelength filter (e.g., 127, 129, or 131) or polarizer (e.g., 133 or 135) does not contact lenses 103).

Although FIGS. 1B through 1F show all wavelength filters and/or polarizers having the same or similar location in relation to openings of filter array or slots of combined array, each of the wavelength filters and/or polarizers according to some embodiments may have different placements in relation to openings within the same filter array or to slots within the same combined array. According to some embodiments, different wavelength filters and/or polarizers within a single filter array may be arranged in any combination of arrangements shown in FIGS. 1C through 1F. For example, one or more wavelength filters and/or polarizers of the filter array may be positioned upstream of openings of filter array (or slots of combined array) while one or more other wavelength filters and/or polarizers positioned downstream of openings of filter array (or slots of combined array). Furthermore, according to embodiments of the present invention, no particular order of wavelength filters and/or polarizers within the plane of a single filter array is required. For example, wavelength filters do not need to be grouped apart from polarizers or other elements within a single filter array (i.e., they may be intermixed in the filter array).

Figure 1G:
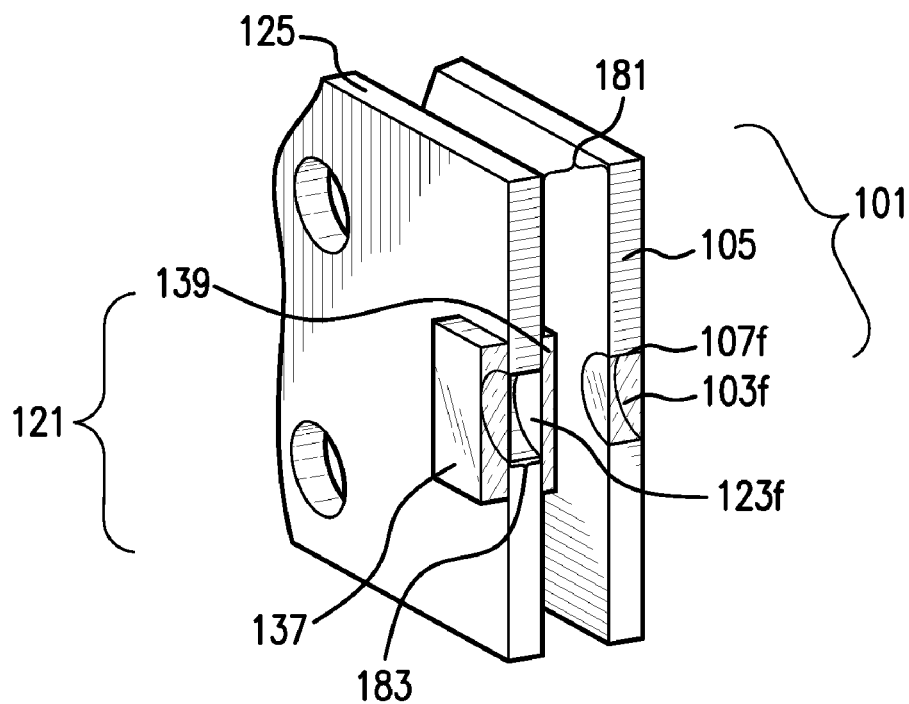
FIG. 1G is a perspective view of a portion of a multi-aperture system showing a portion of a filter array and a portion of a lenslet array with a wave plate located on the upstream side of an opening in the solid matrix of the filter array and a linear polarizer located on the downstream side of the same opening.

The filter array of a multi-aperture system according to embodiments of the present invention may further comprise at least one quarter-wave plate in combination with a linear polarizer oriented at 45° relative to the polarization state of incident light to determine the circular polarization state of light reflected by the retina of a subject. For example, a quarter-wave plate is shown in FIG. 1G as being positioned on the upstream side of an opening 123f of solid matrix 125 of filter array 121 with its associated linear polarizer 139 positioned on the downstream side of the opening 123f of solid matrix 125 of filter array 121 with quarter-wave plate and linear polarizer shown as separated by a length 183 corresponding to the length of opening 123f. Solid matrix 125 of filter array 121 is further shown as being separated from solid matrix 105 of lenslet array 101 by a distance 181, which may be small as long as linear polarizer 139 does not physically contact lens 103f of lenslet array 101.

However, it is not necessary that quarter-wave plate and its associated linear polarizer be located on opposing sides of an opening of the solid matrix of a filter array. In fact, quarter-wave plate and linear polarizer may be in direct contact as long as quarter-wave plate is located upstream of linear polarizer. According to some embodiments, for example, a conjoined quarter-wave plate and linear polarizer may be positioned together on either the upstream or downstream side of opening of solid matrix of filter array. In reference to FIG. 1F, for example, a conjoined quarter-wave plate and linear polarizer may both be positioned on the upstream side of a slot of the solid matrix of a combined array.

According to some embodiments of the present invention, in addition to measuring at least three wavelengths for determining oxygen saturation directly and at least four measurements of polarization states, at least three additional wavelength measurements may be made to model and control for the effect of melanin on light reflected by the retina of a subject. By modeling the melanin content and polarization state of light within the two-dimensional area of the retina imaged by the multi-aperture system, the accuracy of the oxygen saturation calculation may be improved. Although there is a linear relationship between melanin content and absorbance between about 550 nm and about 600 nm, this range is typically avoided when determining melanin content apart from oxygen saturation because of the higher hemoglobin absorbance in this range. Instead, wavelengths between about 600 nm and about 700 nm are typically chosen for measurement and modeling of melanin content.

Figure 2A:
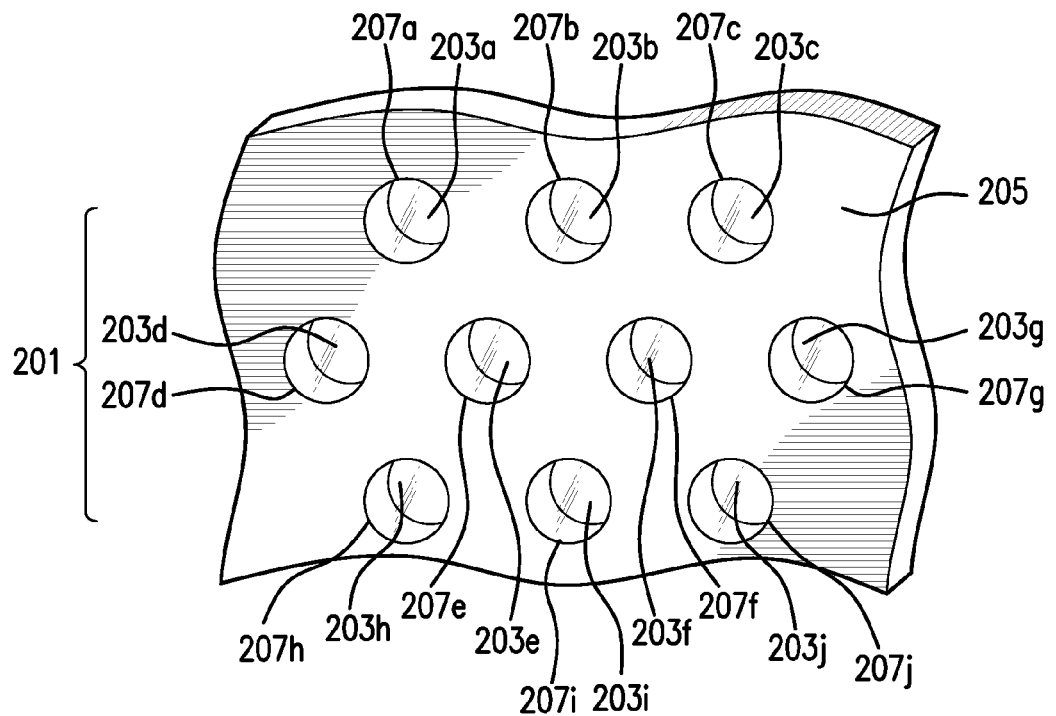
FIG. 2A is a cut-away perspective view of an exemplary lenslet array of a multi-aperture system according to embodiments of the present invention having at least ten (10) lenses.
Figure 2B:
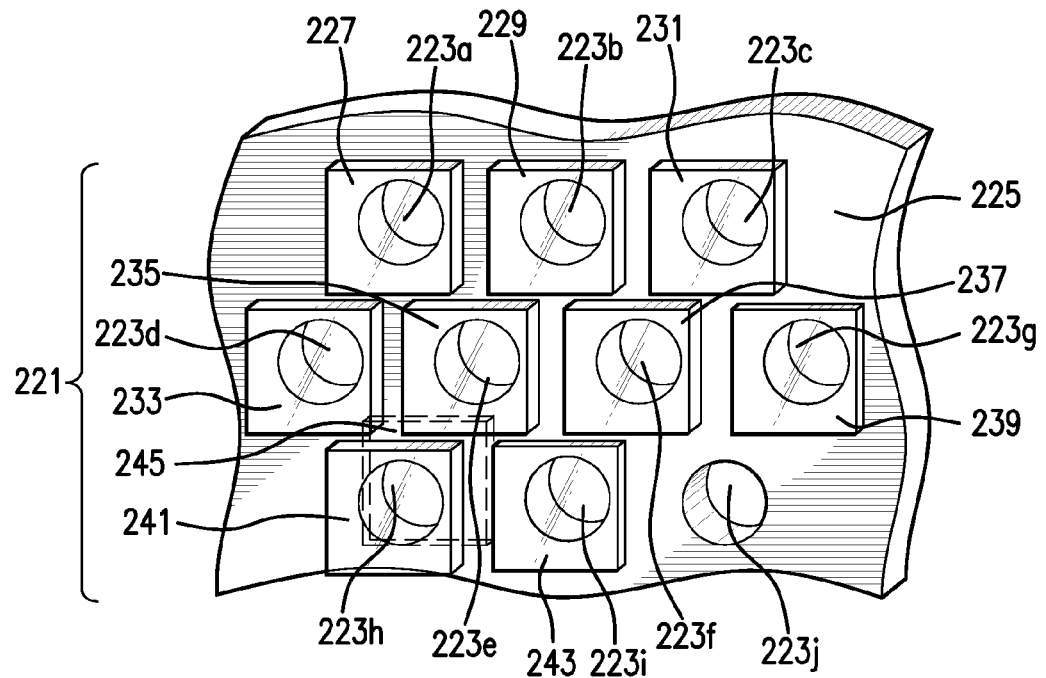
FIG. 2B is a cut-away perspective view of an exemplary filter array of a multi-aperture system according to embodiments of the present invention with openings of filter array separately covered by (i) at least three wavelength filters for oxygen measurement, (ii) at least three wavelength filters for measurement of melanin content, (iii) at least two linear polarization filters, (iv) at least one combination of a wave plate and a linear polarizer, and (v) at least one opening that is uncovered (i.e., no polarizer, filter, or wave plate).

As shown in FIGS. 2A and 2B, a multi-aperture system according to some embodiments of the present invention may comprise a lenslet array 201 as shown in FIG. 2A having at least ten lenses 203(a-j). Such lenses are shown inside a solid matrix 205 of a lenslet array 201. However, the number of lenses may be greater than ten, and the size of the solid matrix (shown in cut-away in FIG. 2A) may vary. The multi-aperture system may further comprise a filter array 221 as show in FIG. 2B having at least three wavelength filters (e.g., 227, 229, or 231) for measuring oxygen saturation, at least three additional wavelength filters for measuring melanin content (e.g., 233, 235, or 237), and at least four openings for making polarization measurements, wherein the at least three wavelength filters (e.g., 227, 229, or 231) for measuring oxygen saturation are each different than the at least three additional wavelength filters for measuring melanin content (e.g., 233, 235, or 237). In general, the arrangement shown in FIGS. 2A and 2B is similar to FIGS. 1A and 1B except for the addition of the at least three additional wavelength filters for measuring melanin content (e.g., 233, 235, or 237).

According to embodiments of the present invention, to allow light passing through each opening of a filter array of a multi-aperture system to also pass through a corresponding lens of a lenslet array of the multi-aperture system, the openings in the solid matrix of the filter array should be spatially arranged to correspond to the positioning and/or arrangement of lenses in solid matrix of lenslet array. This will allow sufficient light reflected by the retina of a subject to pass through each of the at least ten openings of the filter array, pass through most or all of the diameter of a corresponding lens of the lenslet array, and become projected into a plurality of two-dimensional images onto the detection surface of a detection system. For example, the at least ten lenses 203(a-j) of lenslet array 201 are shown in a similar arrangement as openings 223(a-j) of filter array 221. When the filter array and the lenslet array are juxtaposed and aligned, light passing through all of the pairs of openings in the filter array and lenses of the lenslet array will create a plurality of two-dimensional images corresponding to light reflected by roughly the same area of the retina of a subject. For example, by juxtaposing filter array 221 and lenslet array 201 shown in FIGS. 2A and 2B, at least ten two-dimensional images may be generated, which correspond to light reflected from roughly the same area of the retina of a subject. By generating a plurality of images that correspond to the same physical coordinates of the retina of a subject, each image may be separately analyzed to determine different components and characteristics of light reflected by the same location of the retina of a subject.

According to embodiments of the present invention, the at least three wavelength filters for measuring oxygen content as part of a filter array having at least ten openings may be selected as described above. In addition, the at least three wavelength filters for measuring melanin content (e.g., 233, 235, or 237) may be selected from those having peak transmission wavelengths between about 600 nm and about 700 nm, such as wavelength filters having the following approximate peak transmission wavelengths: 600, 610, 620, 630, 640, 650, 660, and 680 nm. As described above, each of the wavelength filters chosen for use in determining melanin content should have an approximate peak transmission wavelength that is different than those for the at least three wavelength filters for measuring oxygen content.

According to embodiments of a multi-aperture system having a filter array comprising at least ten openings, wave plates and/or linear polarizers of filter array that may be used for making polarization measurements may be selected as described in conjunction with FIGS. 1A and 1B. In general, four polarization measurements may be made. For example, FIG. 2B provides for at least four polarization measurements made by a filter array 221 having (i) a first linear polarizer 239 oriented at 45° relative to the polarization state of incident light, (ii) a second linear polarizer 243 oriented at 90° relative to the polarization state of incident light, and (iii) a quarter-wave plate 241 located upstream relative to an associated third linear polarizer 245 oriented at 45° relative to the polarization state of incident light. In addition, light passing through an uncovered opening 223j of filter array 221 may be used as a basis for comparing images of reflected light through the first linear polarizer 239 and second linear polarizer 243 and/or the quarter-wave plate 241 in combination with its associated third linear polarizer 245. Such information may be used to determine the Stokes parameters and vector. As an alternative to leaving at least one of the openings of the filter array uncovered, at least one of the openings of the filter array may instead be covered with a neutral density filter (not shown).

Alternatively, according to some embodiments, a fourth linear polarizer (not shown) oriented at 0° relative to the linear polarization state of incident light associated with an opening of a filter array of a multi-aperture system may be used in place of (or in addition to) an uncovered opening in the filter array. Similarly to the unaltered image generated by passing reflected light through the uncovered opening, images created by reflected light passing through the linear polarizer at 0° may also be used as a basis of comparison for light passing through the first and second linear polarizers oriented at 45° and 90° relative to the polarization state of incident light. This information may again be used to determine the Stokes parameters and vector.

Figure 2C:
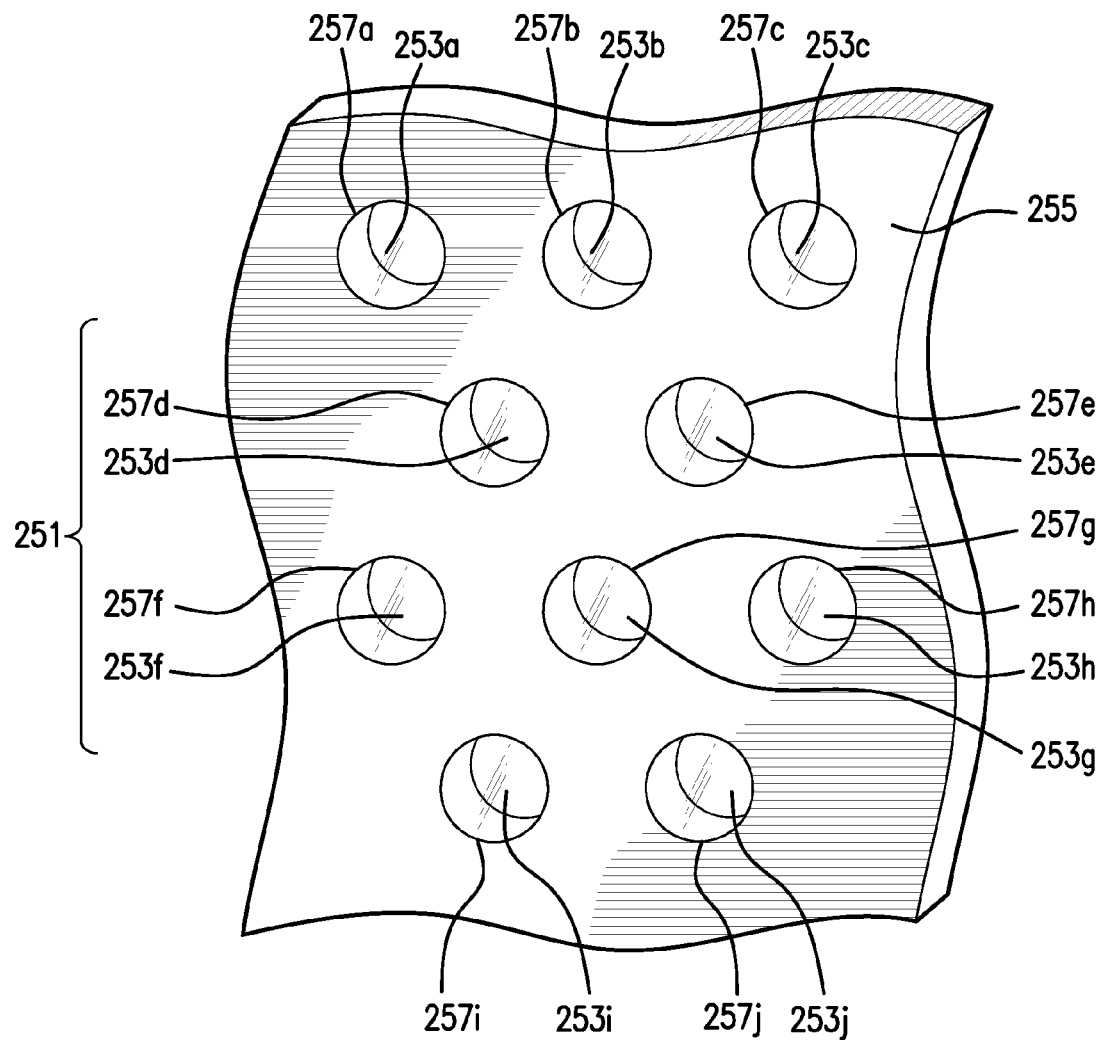
FIG. 2C is a cut-away perspective view of an exemplary lenslet array of a multi-aperture system according to embodiments of the present invention having at least ten (10) lenses with an alternate arrangement compared to FIG. 2A.

The at least ten lenses 203(a-j) of lenslet array 201 shown in FIG. 2A (as well as filter array 221 shown in FIG. 2B) are shown in a 3:4:3 layout or arrangement as a way of compacting their arrangement. However, lenses may have any arrangement and relative spacing in the lenslet array that would be appropriate. Embodiments of the present invention may have lenses arranged in the lenslet array to attempt to maximize or increase usage of the detection surface (not shown) of a detection system (i.e., to minimize the amount of unused or wasted space on the detection surface of a detection system) used for visualization or detection of a plurality of retinal images projected by the lenslet array of a multi-aperture system. Other arrangements may be possible that also attempt to maximize or increase usage of the detection surface (not shown) of a detection system. For example, FIG. 2C shows an alternative 3:2:3:2 arrangement for the at least ten lenses 253(a-j) of a lenslet array 251.

Each column and/or row of lenses in the lenslet array may be positioned to fit a greater number of lenses within a given area of the solid matrix of the lenslet array. Lenses in one row or column may be positioned approximately on a midline between two lenses of an adjacent row or column. For example, lens 203e is shown in FIG. 2A positioned approximately on a midline between lenses of an adjacent row or column (e.g., 203a and 203b; or 203a and 203h). The exact spacing between adjacent lenses in lenslet array may vary as long as the plurality of lenses of lenslet array allows for most or all of the plurality of retinal images to be projected onto the detection surface of a detection system. For example, the spacing between lenses (measured center-to-center) may be from about 6 mm to about 10 mm. However, some overlap of two-dimensional images projected by lenslet array of a multi-aperture system onto the detection surface of a detection system may be tolerated.

Lenses of a lenslet array may be any appropriate type of lens as briefly described above in conjunction with FIG. 1A. In addition, as described above, lenses 203(a-j) of lenslet array 201 may either be directly inserted in slots 207(a-j) of solid matrix 205 of lenslet array 201 as shown in FIG. 2A, or alternatively by using an additional piece (e.g., a plastic ring) of larger diameter (not shown) that may in turn be directly attached or mounted inside slots of solid matrix of lenslet array.

Figure 3:
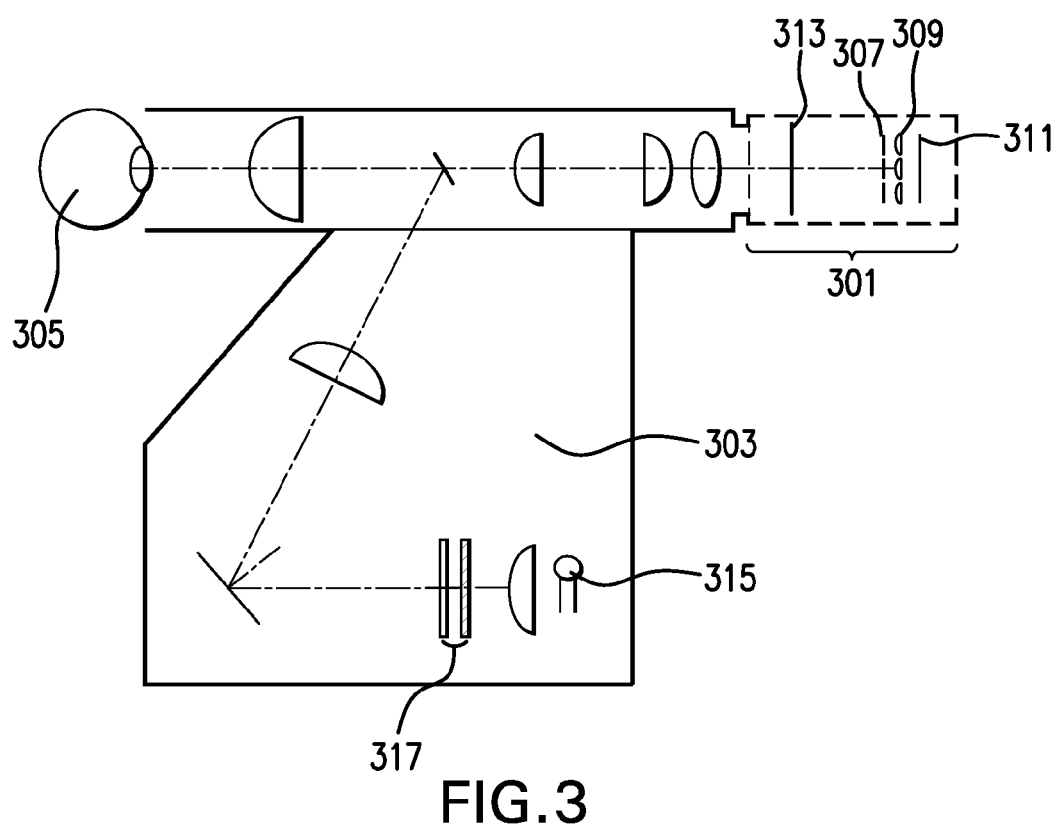
FIG. 3 is a schematic diagram of an exemplary layout of a multi-aperture system containing a lenslet and filter array attached to a standard fundus opthalmoscope similar to embodiments of the present invention.

According to embodiments of the present invention, FIG. 3 shows an example of a multi-aperture system 301 interfaced with an optical device 303 for viewing light images reflected by the retina of an eye 305 of a subject. For example, the multi-aperture system may be positioned at the exit pupil of an optical device. Such multi-aperture system 301 is shown as comprising a filter array 307 and a lenslet array 309 for projecting a plurality of two-dimensional images corresponding to the same spatial coordinates of the retina of a subject onto the detection surface 311 of a detection system, such as a camera, CCD, film, etc. Generally speaking, a larger detection surface 311 of the detection system is preferred to allow for greater resolution of each image and/or a greater number of images to be acquired. Alternatively, a combination of smaller CCD cameras may be used as a detection system. For example, each individual CCD camera of the detection system may be dedicated to the capture of one or more of the plurality of images.

The retina may be illuminated by a lamp source providing a broad spectrum of incident light, such as Xenon, white LED, Tungsten, etc. High- and low-pass color filters 317 may be placed in front of the lamp source 315 to limit the spectrum of incident light used to illuminate the retina. For example, a high-pass yellow filter with a cutoff wavelength of 480 nm and/or a low-pass IR filter with a cutoff wavelength of 700 nm may be used. A linear polarizer (not shown) may also be placed in the path of incident light to allow for the polarization state of reflected light to be determined as described herein.

In addition, a multi-aperture screen 313 may be inserted in the path of reflected light in the multi-aperture system 301 to reduce the depth of field and improve image quality (although light intensity will be decreased). The number of apertures in the multi-aperture screen 313 may correspond to the number of lenses in the lenslet array 309. Multi-aperture screen may be placed at some distance from filter array 307 and lenslet array 309 (e.g., greater than or equal to about 50 mm). However, this effect could alternatively be achieved without the multi-aperture screen 313 through the use of additional lenses (not shown).

EXAMPLES

Example 1

Material and Methods

Figure 4:
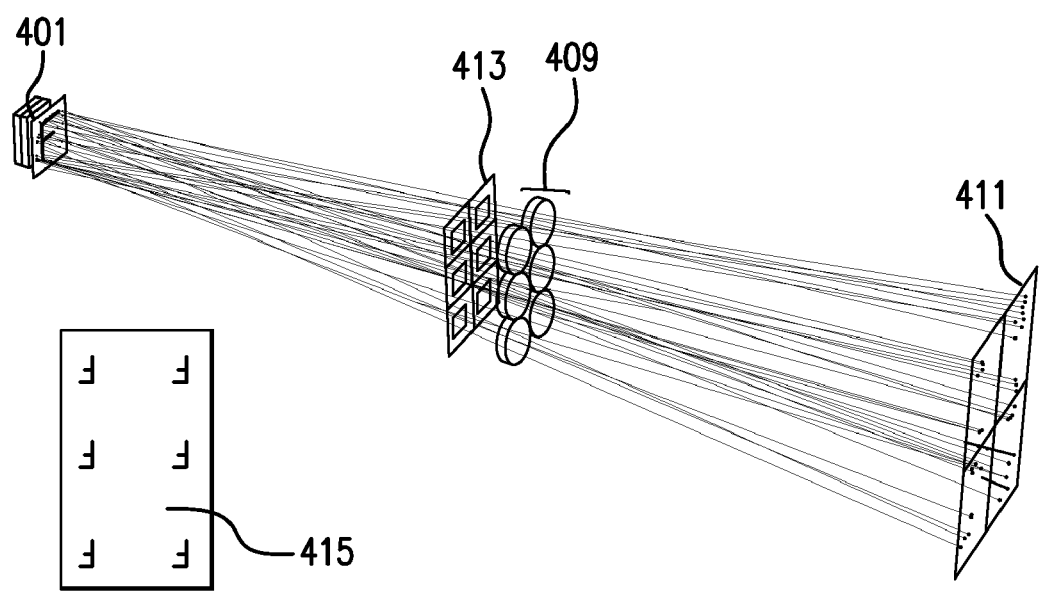
FIG. 4 is a ray tracing diagram showing an exemplary projection of a divided set of images using a 2×3 (6 lenslet) array with insert showing the resulting six divided images.

A schematic representation of a multi-aperture system containing a lenslet array according to some embodiments of the present invention is shown attached to a fundus opthalmoscope in FIG. 3. The system may be composed of a commercially available fundus opthalmoscope (e.g., TRC-FET, Topcon Paramus, N.J.) or other optical device along with a custom built multi-aperture camera. A detection system, such as a 12 bit monochromatic digital camera (Lumenera, North Andover, Mass., USA), may be interfaced with the custom made lenslet array. The distance from the detection system, such as the surface of a CCD, to the plane of the lenslet array may be adjusted with a micro-positioning stage and may be about 0.5 mm. The size of the CCD may be about 10.2 mm×8.3 mm (i.e., 1392 pixels×1040 pixels). A filter array may be positioned in front of the lenslet array so that each of the images formed has a distinct wavelength. A multi-aperture (focusing) screen (e.g., Ritz Camera, Irvine, Calif., USA) in front of the array, such as about 55 mm from the filter array, may be used to decrease the depth of field of the lenses and to minimize the effect of the fundus camera light source. The focusing screen may also be adjustable with a positioning stage, thus providing a crude magnification variation. The camera system may be adapted to a fundus opthalmoscope or other optical device so that the image formed by the fundus is projected by the lenslet array into multiple images onto a detection system, such as a CCD, as shown in FIG. 4.

Although the focusing screen reduces the amount of light reaching the imager, it has been shown to be a very efficient way to reduce the depth of field of the multi-aperture camera without the addition of any other optical elements. This may have the advantage of keeping the imager compact and reasonably light. A lenslet array may be built with six plano-convex lenses (LightPath Optical Instrumentation, Shanghai, China) supported by a custom-made aluminum plate. The lenses may be about 2 mm in diameter and have a numerical aperture equal to about 0.15 and an effective focal length of about 5 mm. Lens to lens separation may be about 2.5 mm. The filters may be about 2.5×2.5 mm narrow band filters (e.g., 20 nm FWHM, Newport, Irvine, Calif., USA). However, the 575 nm filter may be circular with about a 3 mm diameter. Different combination of filter arrays may be tested. For example, a quintuplet of 540, 560, 576, 600, and 680 nm, or sextuplets of 560, 575, 600, 630, 650, and 660 nm or 540, 560, 575, 600, 650, and 660 nm may be used in these examples.

The choice of wavelengths may be guided by several factors including information from (1) previous publications (See, e.g., Hammer et al., "Optical properties of ocular fundus tissues—an in vitro study using the double-integrating-sphere technique and inverse Monte Carlo simulation," *Phys. Med. Biol.* 40:963-78 (1995), the entire contents and disclosure of which are hereby incorporated by reference), (2) Monte Carlo simulations of light travel into retinal tissue (See, e.g., Preece et al., "Monte Carlo modeling of the spectral reflectance of the human eye," *Phys. Med. Biol.* 47:2863-2877 (2002); and Hammer et al., "Light Paths in Retinal Vessel Oxymetry," *IEEE Trans Biomed Eng* 48(5):592-8 (2001), the contents and disclosure of which are hereby incorporated by reference in their entirety), and (3) commercial availability (e.g., the typical 586 nm isosbestic wavelength is not readily available in a small format). For example, several investigators have pointed out that the impact of melanin is lower for shorter wavelengths (See, e.g., Delori, (1988), supra; Schweitzer et al., (1995), supra; and Drewes et al., (1999), supra), and algorithms for oxygen saturation, such as the one proposed in Delori, (1988), supra, generally work best in a range from about 500 nm to about 600 nm. For this reason, the multi-aperture filter arrays according to embodiments of the present invention may include filters for at least three wavelengths within this range. Longer wavelength ranges, such as from about 600 nm to about 700 nm, may be useful in establishing melanin concentration. See, e.g., Sarna, H. M., "The physical properties of melanins," In *The Pigmentary System*, R. E. Nordlund, V. J. Hearing, R. A. King and J. P. Ortonne, Eds. (Oxford University Press, 1998), p. 439-450, the entire contents and disclosure of which are hereby incorporated by reference. Therefore, filters for wavelengths of light within such range may also be included in the filter array according to embodiments of the present invention. Indeed, due to the simple construction of the lenslet array apparatus according to embodiments of the present invention, filter arrays may be easily replaced, allowing for quick evaluation according to different models comprising different combinations of wavelength and/or polarization sets.

The filter array may be positioned in front of the lenslet array so that the distance between each lens and its corresponding filter is small, such as less than about 0.2 mm. A modification to the optical device, such as a fundus opthalmoscope or slit lamp, which may be connected to a multi-aperture system according to embodiments of the present invention, may be the addition of filters (e.g., two filters) to limit the incident light source and select for wavelength ranges of light that may be relevant to determining oxygen saturation. For example, one filter may be a high pass yellow filter with cutoff wavelength of about 480 nm, and a second filter may be a low pass IR filter with cutoff wavelength about 700 nm. An example ray tracing of a multi-aperture camera embodiment may be obtained with the Rayica software package (Optica Software, Champaign, Ill.) with filters simulated as square apertures as shown in FIG. 4. The projection of a letter "F" 401 through a multi-aperture system comprising a multi-aperture screen 413 and lenslet array 409 is shown. In this figure, the distance between the lenslet array 409 and the detection surface 411 of detection system (e.g., CCD) is exaggerated for clarity. No filter array is shown in this figure. The insert 415 is provided to show the multiple "F" images projected by the multi-aperture system.

1. System Calibration

The multi-aperture system according to embodiments of the present invention may be calibrated using different color standards, such as three NIST traceable Spectralon standards (Labsphere, North Sutton, N.H., USA) of different colors. Such reflection standards may be located at the entrance pupil of a multi-aperture system in the same approximate location as where a patient would place his eye as noted in FIG. 3. For example, images of the standard may be captured by a multi aperture system with an exposure time of about 200 ms. A "dark" image may also be captured by keeping the light source off during the exposure time, such as about 200 ms, and this image may be subtracted from images with the light source on. The image of a "white" 80% reflectance standard may also be captured (e.g., with a 200 ms exposure time), and total reflectance may be calculated as:

$$R(x, y, \lambda) = 80 \cdot \frac{R_{color}(x, y, \lambda) - \text{dark}}{R_{white}(x, y, \lambda) - \text{dark}} \quad (6)$$

Figure 5:
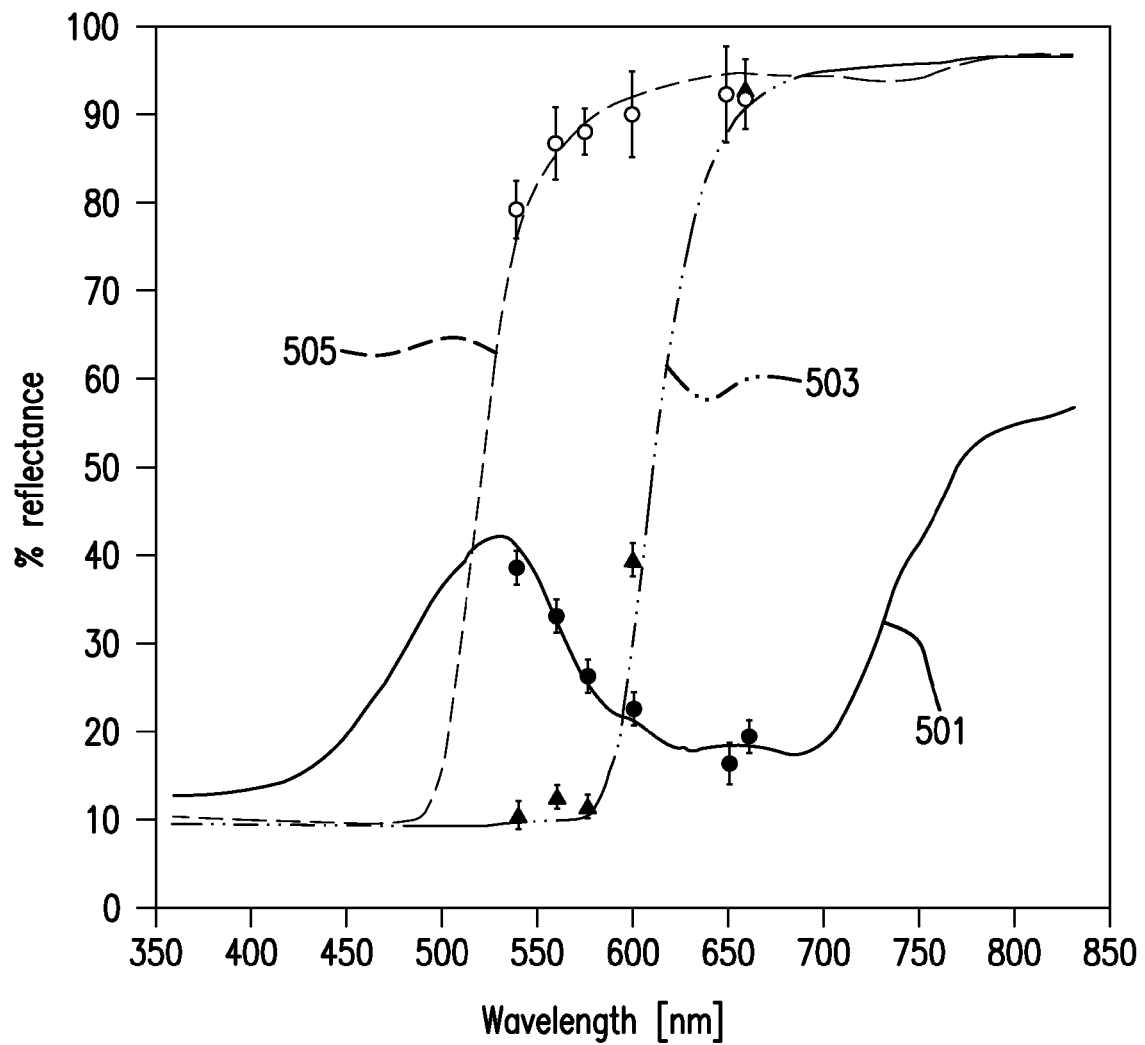
FIG. 5 is a plot showing the calibration of a multi-aperture camera using three different Spectralon colored standards.

In this example, each of the six identical sub-images may be generated at six different wavelengths by a multi-aperture filter and lenslet array. In order to quantify the total reflectance from the color Spectralon, a region of interest (e.g., about 20×20 pixels) may be selected on each of the six sub-images. Results compared with NIST traceable values are shown in FIG. 5. In FIG. 5, solid line (-) 501 corresponds to reflectance values for a green standard with solid circle symbols providing experimentally reflectance values for the green standard; the first dashed line (- • • -) 503 corresponds to reflectance values for a red standard with triangle symbols providing experimentally reflectance values for a red standard; and the second dashed line (- - -) 505 corresponds to reflectance values for a yellow standard with open circle symbols providing experimentally reflectance values for a yellow standard.

The correlation coefficients were R=0.997 for the red data, R=0.997 for the yellow data, and R=0.983 for the green data. The camera may also be tested for linearity, and the amounts of camera exposure may be kept within the linear range of the camera for all subsequent measurements.

2. In Vitro Testing

Figure 6:
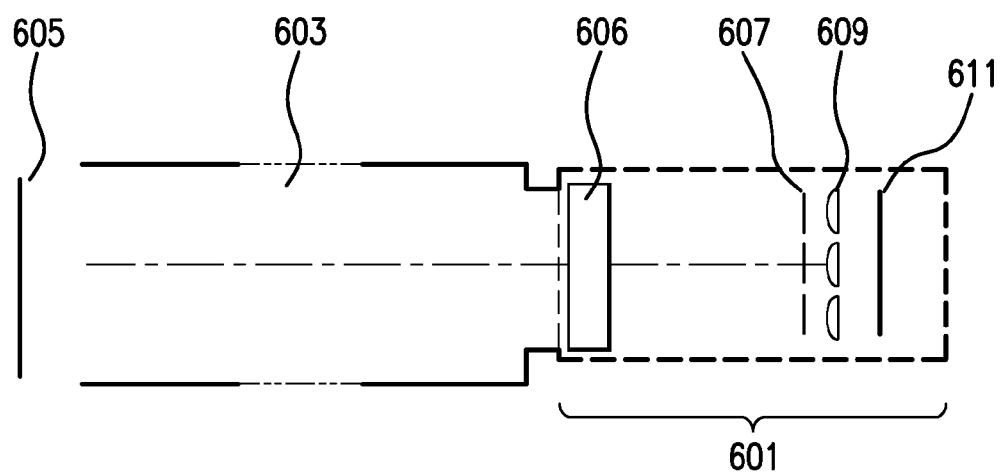
FIG. 6 shows a diagram of an experimental layout of a multi-aperture system containing a lenslet array and a filter array in a transmission mode for the analysis of a standard located at the entrance pupil of a fundus opthalmoscope and a cuvette containing a hemoglobin and water mixture located at the exit pupil.

In vitro experiments may be conducted on solutions of human hemoglobin (Sigma, St Louis, Mo.) and water. For example, about 10 mg of hemoglobin may be diluted in about 10 ml of DI water and thoroughly stirred. Using such hemoglobin solutions, two principal experimental layouts may be considered: (a) transmission, and (b) reflection. With a transmission modality (as shown in FIG. 6), an approximately 1 mm thick quartz cuvette 606 filled with a hemoglobin solution may be positioned at the exit pupil of a fundus opthalmoscope 603. A multi-aperture system 601 may also be placed at the exit pupil of the fundus opthalmoscope 603, and the cuvette 606 may be placed inside the multi-aperture system 601 as shown near the exit pupil. The multi-aperture system in this transmission modality is shown with a filter array 607 and a lenslet array 609 for projecting multiple images onto a detection surface 611 of a detection system.

Figure 7:
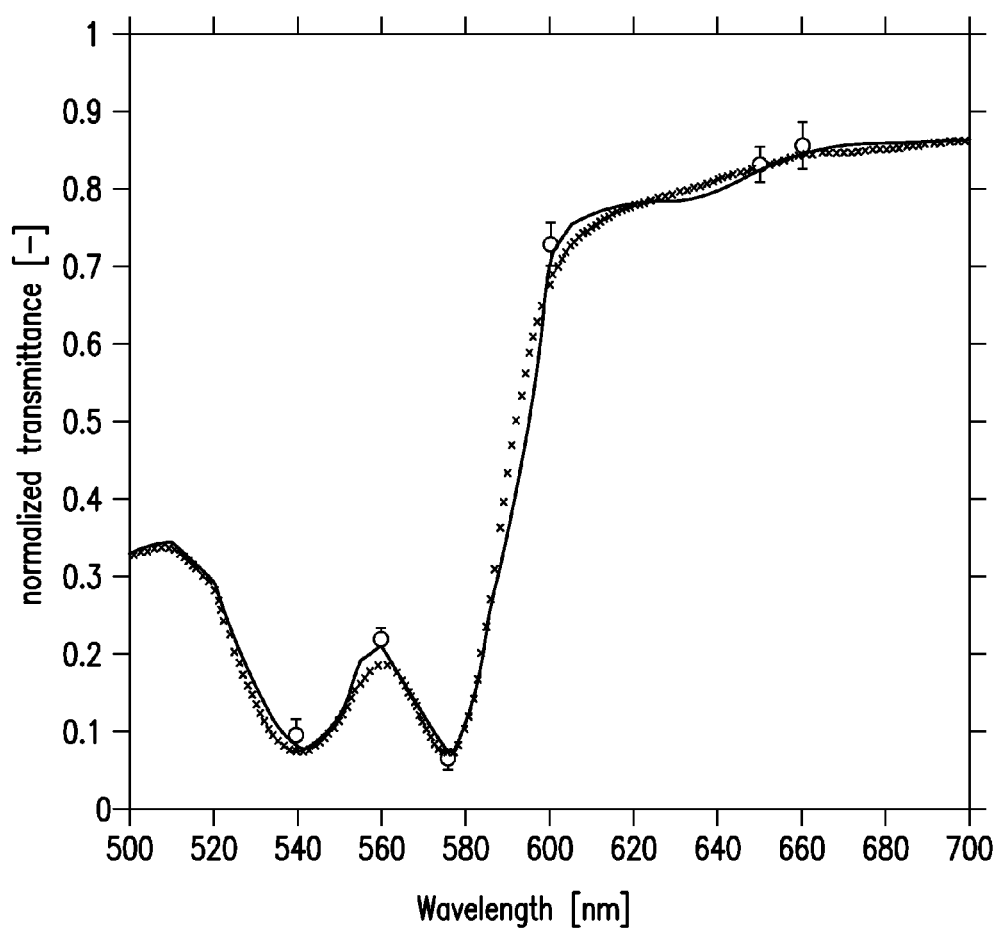
FIG. 7 is a plot showing the transmission curve through a cuvette containing a mixture of water and hemoglobin with the solid line corresponding to the theoretical model of equation 7 obtained using tabulated values of oxygenated and deoxygenated hemoglobin, with x symbols showing the experimental results obtained with a spectrophotometer, and with circles (o) showing the average pixel values obtained using an embodiment of a multi-aperture system of the present invention.

For the reflectance modality, a reflectance standard 605 may be placed at the entrance pupil of the fundus opthalmoscope 603 that may reflect 99% of the incident light back toward the multi-aperture system or camera. Reflected light may travel through the cuvette 606 before reaching the lenslet array 609 and ultimately the detection system (e.g., CCD). With this experiment, the focusing screen may be removed. Wavelength sensitive images of light transmission through the cuvette 606 may be captured and compared to measurement of absorption by the same solution in the cuvette obtained using a bench-top spectrophotometer (Ultrospec 3000, Pharmacia Biosystems, DK). Some results obtained with oxygenated hemoglobin ($SO_2$=98%) are shown in FIG. 7.

This scenario may be modeled with Beer's Lambert law:

$$T = A \cdot \exp[-[s \cdot \mu_{\alpha Oxy} - (1-s) \cdot \mu_{\alpha DeOxy}] \cdot L] \quad (7)$$

where T stands for transmission, s for oxygen saturation, L is the cuvette thickness, and $\mu_{aoxy}$ and $\mu_{aDeOxy}$ are the absorption coefficients for oxygenated and deoxygenated hemoglobin obtained from known values for hemoglobin. See, e.g., Harris et al., (2003), supra.

Figure 8:
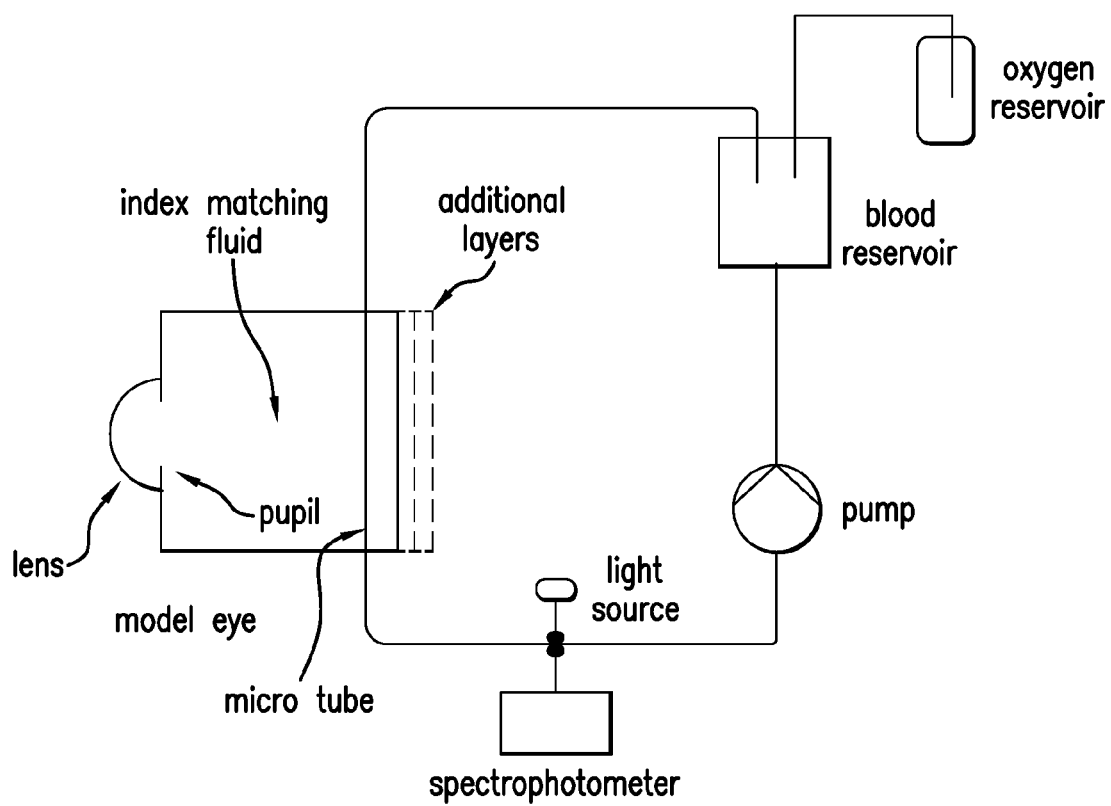
FIG. 8 is a schematic diagram showing an in vitro eye model used for testing and calibration.

A second modality based on reflection may be conducted on a simplified eye model depicted in FIG. 8. A similar eye model has been used previously for calibration purposes. See, e.g., Drewes et al., (1999), supra. For example, an eye model may be constructed using a 5×5 cm black Delrin® case. A micro-tube, such as a 150 μm inner diameter micro-tube made of, for example, Teflon, may be used to simulate a vessel in the retina and may be positioned in front of a thick Spectralon slab (99% reflective) to represent the highly backscattering sclera. A dilated pupil may be reproduced with a hole (e.g., 6 mm) in the front casing wall, and a plano-convex lens on top of the pupil may be used to mimic the crystalline lens of a real eye. The casing may be filled with index matching fluid to minimize eye to vessel interface and undesirable lensing effects to simulate the vitreous humor, and the vessel may be connected to a solenoid-actuated micropump.

The micropump may maintain a pulsed flow of about 9 ml/min, a value close to human retinal flow. Oxygen content of vessel hemoglobin may also be controlled through a small oxygen reservoir and flow-meter. However, the oxygen reservoir was not used in this example. Instead, several reduced levels of hemoglobin were obtained by adding different quantities of Sodium Hydrosulfite (Sigma, St. Louis, Mo.) to the hemoglobin solution. Experiments were repeated four times for each oxygen level. Calibration may be achieved with a spectrometer connected to the vessels via fiber optics to measure the absorbances of the re-circulating fluid. The eye model may be located at the entrance pupil of an optical device associated with a multi-aperture system in place of a patient's eye.

Images of light backscattered from the model eye may be analyzed with the same process described above for the transmission experiment with the reflectance values on the vessel normalized by reflectance of an area near the vessel. This particular normalization procedure may be used to eliminate the effect of the background. See, e.g., Schweitzer et al., (1995), supra.

Two different models may be used to calculate oxygen saturation values in both scenarios. According to a first model, a three-wavelength algorithm, such as proposed by Delori, (1988), supra, may be used. According to this approach, oxygen saturation in a retinal vessel may be calculated using tabulated values of extinction coefficient of oxygenated and deoxygenated hemoglobin as well as experimentally obtained values of optical density in the retina at three different wavelengths. The use of three wavelengths (instead of two) improves the calculation of oxygen saturation by taking the effects of light scattering into account. An operator (RP) relating the three optical densities $D^{\lambda 1}$, $D^{\lambda 2}$ and $D^{\lambda 3}$ obtained at three different wavelengths may be used (for example, in Delori, λ1=569, λ2=558 and λ3=586 were used):

$$RP = (D^{\lambda 1} - D^{\lambda 2})/(D^{\lambda 1} D^{\lambda 3}) \quad (8)$$

Oxygen saturation may also be defined as:

$$SO_2 = 100 \cdot \frac{(\varepsilon_{Hb}^{\lambda 1} - \varepsilon_{Hb}^{\lambda 2}) + (\varepsilon_{Hb}^{\lambda 3} - \varepsilon_{Hb}^{\lambda 1}) \cdot RP}{(\Delta^{\lambda 2} - \Delta^{\lambda 1}) + (\Delta^{\lambda 1} - \Delta^{\lambda 3}) \cdot RP} \qquad (9)$$

where $\Delta^{\lambda'} = (\varepsilon_{HbO_2}{}^\lambda - \varepsilon_{Hb}{}^\lambda)$, D is the optical density obtained experimentally, and $\varepsilon_{HbO_2}{}^\lambda$ and $\varepsilon_{Hb}{}^\lambda$ are tabulated values of extinction coefficients for oxygenated and deoxygenated hemoglobin. Results from a table-top spectrophotometer may also be analyzed using this model. Since Delori used two isosbestic wavelengths (569 and 586 nm), equation 9 was able to be simplified to eliminate the second term in the denominator. However, it has been shown that isosbestic wavelengths are generally not necessary mathematically. See, e.g., Smith et al., (1999), supra. In this example, two wavelength triplets (i.e., $\lambda 1$=540 nm, $\lambda 2$=560 nm and $\lambda 3$=577 nm or $\lambda 1$=540 nm, $\lambda 2$=560 nm, and $\lambda 3$=600 nm may be used. Wavelengths in the 500 to 600 nm range are often used to measure oxygen saturation in eye oximetry to minimize the effect of melanin absorption.

Figure 9:
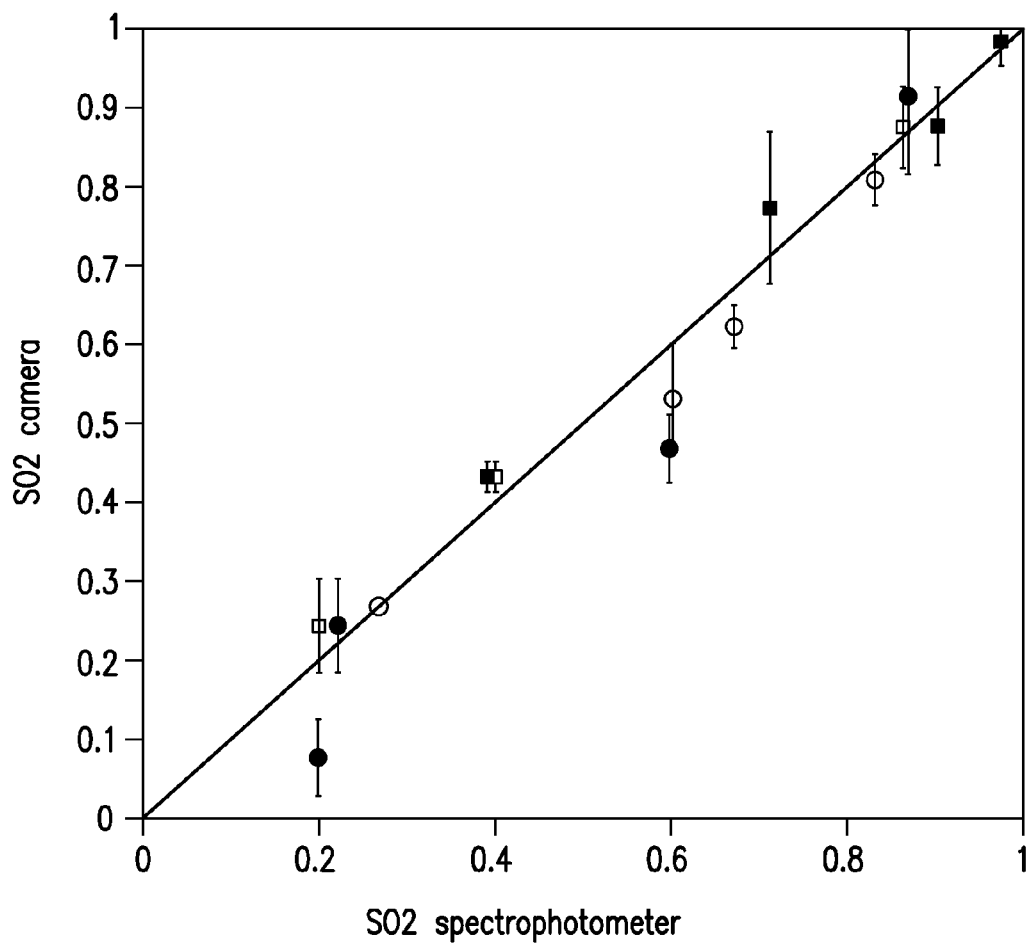
FIG. 9 is a plot showing the correlation between calculated oxygen saturation values obtained using a multi-aperture system versus a spectrophotometer with filled symbols calculated using the Schweitzer model, open symbols obtained using the Delori model; open or filled square symbols from a transmission experiment, and open or filled circular symbols from a reflection experiment.

According to a second model, an algorithm originally proposed by Schweitzer et al., (1995), supra, may be used. This algorithm may keep into account, not only the hemoglobin absorption, but also wavelength-dependent scattering caused by erythrocytes. The optical density of light backscattered from a vessel may be modeled as:

$$D(\lambda) = B + n \cdot \log\left(\frac{1}{\lambda}\right) + b[\varepsilon_{Hb}(\lambda) + s(\varepsilon_{HbO_2}(\lambda) - \varepsilon_{Hb}(\lambda))] \cdot c_{tot} \cdot l \qquad (10)$$

where B and $n \cdot \log(1/\lambda)$ are used to simulate both wavelength independent and wavelength dependent scattering. The term b is an experimental geometry factor, $c_{tot}$ is the total hemoglobin concentration, l is the vessel thickness, and s is oxygen saturation. A least-squares mechanism using the Nelder-Mead simplex method and four fitting parameters (B, A=$c_{tot}$lb, s, and n) may be used to fit the model to the data. See, e.g., Nelder et al., "A simplex method for function minimization," *Computer J.* 7:308-313 (1965), the entire contents and disclosure of which are hereby incorporated by reference. It is noted that this algorithm works best with a large number of wavelengths. The only constraint to the model may be that s and n may have to be between 0 and 1. The spectra collected with the fiber optic-based spectrophotometer may also be analyzed with the two models above. FIG. 9 shows a comparison of results obtained with a multi-aperture system or camera and with a spectrophotometer calibration.

These experiments show that a multi-aperture camera containing a lenslet array is well suited for measuring oxygen saturation. However, a least square fit may not ideally fit a non-linear model, such as the one by Schweitzer et al., and other known techniques may be used. In addition, a simplified model of a human eye does not consider the choroid and retinal pigment epithelium (RPE) effect on the remitted spectrum.

3. Image Registration

Figure 10:
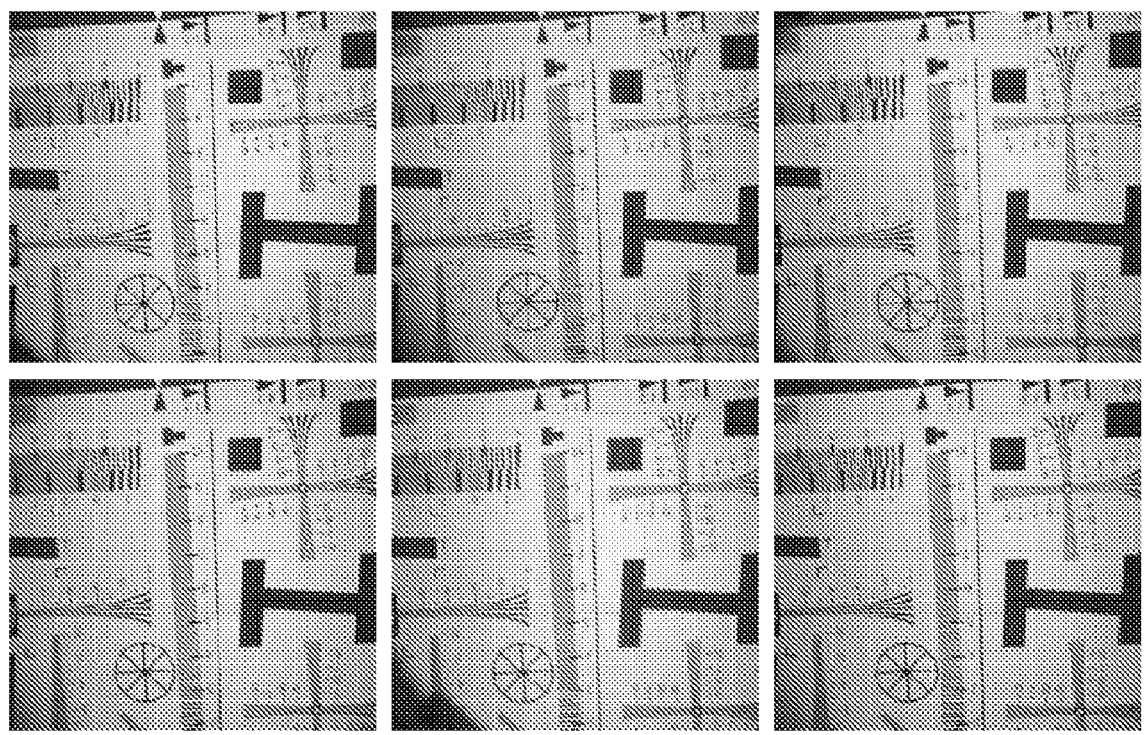
FIG. 10 shows a set of six repeated images generated from a single IEEE target reflection standard used for manual registration by choosing a common region of interest from the six repeated images.

The registration of resulting images (e.g., six images) from a multi-aperture system with a lenslet array may be achieved using a resolution target, such as an IEEE full field resolution target (Edmund Optics Inc. Barrington, N.J.). According to this approach, the target may be illuminated, such as with a white light source (Newport Stratford, Conn.), and images of the target acquired by a detection system, such as a camera, of a multi-aperture system. For example, the camera to target distance may be about the same as the screen to camera distance shown in FIG. 3. Registration of the resulting images, such as the six images in FIG. 10, may be done manually or automatically. Once coordinates relative to the registered images are obtained, they may be used for registering in vivo images of the eye.

Modeling Considerations

A difficulty with measuring oxygen saturation in the retina is in the choice of algorithm and/or the analyzing scheme used to capture the complex optical environment of the retina. One advantage of a multi-aperture system based on a lenslet array is its insensitivity to eye movement artifacts as well as its ability to capture images at a greater number wavelengths, polarizations, etc. unlike prior devices. Published algorithms are generally for either 2 to 4 wavelength sets, such as those in Delori, (1988), supra and Drewes et al., (1999), supra, or they use large data sets, such as in Schweitzer et al., (1995), supra. Some investigators have used an Inverse Monte Carlo (IMC) models for this purpose. See, Johnson et al., (2007), supra. However, this type of algorithm is computationally intensive and time consuming, especially in an imaging environment, and is unable to accommodate other types of optical elements, such as polarizers.

On the other hand, a forward Monte Carlo model may be used to quantify the effect of various layers of the retina on remitted light. Peerce et al. have shown that critical parameters that impact measurement of oxygen saturation generally include hemoglobin concentration, melanin variation in the choroids, and density of melanin in the RPE. Therefore, according to embodiments of the present invention, modeling may be restricted to these parameters. See, e.g., Preece et al., (2002), supra.

Monte Carlo simulations may be done using the program MCML (See, e.g., Wang et al., "MCML—Monte Carlo modeling of photon transport in multilayered tissues," *Comput. Methods Programs Biomed.* 47:131-146 (1995), the entire contents and disclosure of which are hereby incorporated by reference), and the retinal layer absorption and scattering coefficient may be sampled using Matlab@ from Hammer et al., "Optical properties of ocular fundus tissues—an in vitro study using the double-integrating-sphere technique and inverse Monte Carlo simulation," *Phys. Med. Biol.* 40:963-78 (1995), the entire contents and disclosure of which are hereby incorporated by reference.

A Monte Carlo simulation may be built with four layers: the neural retinal, the retinal pigmented epithelium (RPE), the choroids, and the sclera having thicknesses of, respectively, 200 µm, 10 µm, 250 µm, and 700 µm. See, e.g., Preece et al., (2002), supra. Analyzed wavelengths may include: 450, 480, 505, 515, 522, 540, 548, 560, 565, 569, 576, 586, 600, 610, 640, and 680 nm. Extinction coefficients for hemoglobin may be taken, for example, from Takahani et al., "Theoretical analysis of diffuse reflectance from a two-layer tissue model," *IEEE Trans. Biomed. Eng.* 26:656-664 (1987), the entire contents and disclosure of which are hereby incorporated by reference, and the melanin absorption coefficient may be taken, for example, from Sarna, H. M., "The physical properties of melanins," In *The Pigmentary System*, R. E. Nordlund, V. J. Hearing, R. A. King and J. P. Ortonne, Eds. (Oxford University Press, 1998), 439-450, the entire contents and disclosure of which are hereby incorporated by reference.

The simulations may be conducted with one million photons from an infinitesimally small beam. The effect of pigmentation in the choroid and RPE is shown for example in FIG. 11. In this simulation, the concentration of melanin in the choroids may be increased in steps of 1, 10, and 50-fold, and in different simulations, the concentration of the RPE melanin may be increased of the same amounts. The effect of melanin in the choroids appears particularly strong at longer wavelengths, while an increase in melanin concentration in the RPE appears to have a more uniform effect across the visible spectrum.

Figure 11:
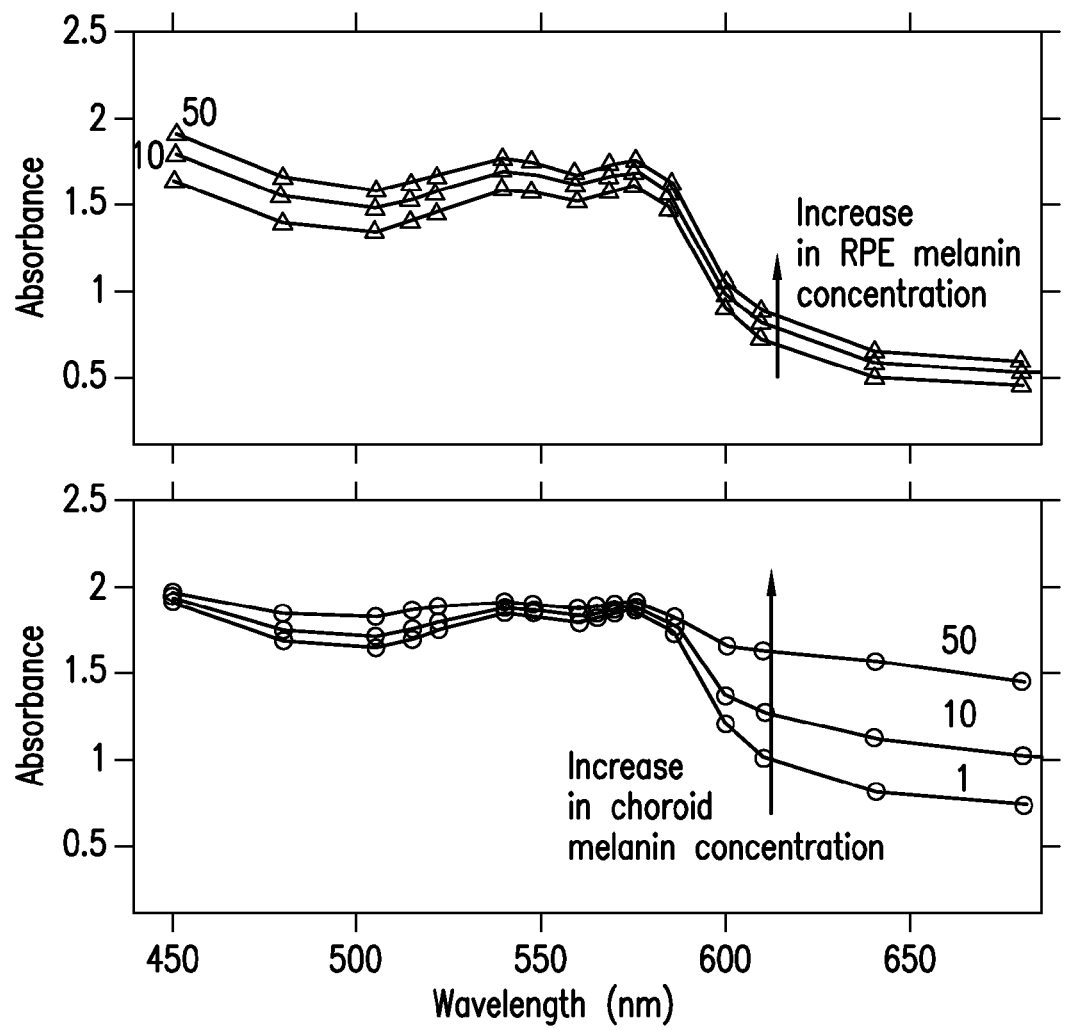
FIG. 11 is a pair of Monte Carlo simulation plots showing the effect of an increase in melanin concentration in the choroid (bottom graph) and RPE (top graph) on the total absorption spectrum of the retina.
Figure 12:
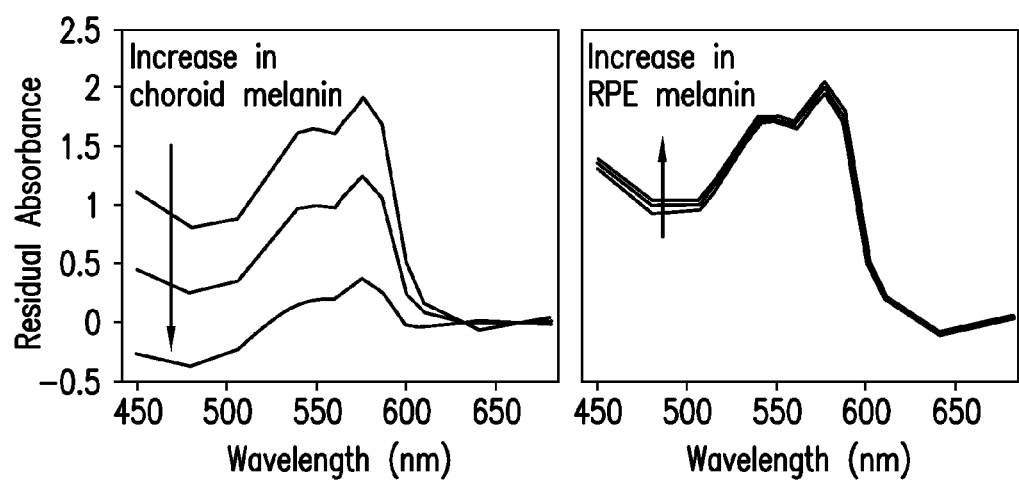
FIG. 12 is a set of plots showing wavelength-dependent residual absorbance according to two schemes where melanin is varied in the choroid only (left panel) or in the RPE only (right panel).

Other approaches to minimize the effect of the melanin absorption have been investigated. For example, it is a known that the extinction coefficient of melanin decreases with increasing wavelength, and in the region between 550 nm and 600 nm, this decay has a constant slope. However, hemoglobin has a high absorption up to 600 nm, while its effect in the 600 nm to 700 nm region is small. The effect of melanin absorption may be reduced with a simple scheme when trying to calculate oxygen saturation in environments where melanin is present. See, e.g., Stamatas et al., "Blood stasis contributions to the perception of skin pigmentation," *J. Biomed. Opt.* 9:315-322 (2004), the entire contents and disclosure of which are hereby incorporated by reference. First, the absorbance of remitted light may be determined, and a line may then be fitted to absorbance values between about 620 nm and about 700 nm. A corrected absorbance may then be calculated by subtracting the line from the total absorbance. Although this scheme is generally not appropriate for shorter wavelengths, it may be used with other wavelength ranges since the extinction coefficient decreases more rapidly at some wavelengths and oxygen saturation may be determined with only a few wavelength measurements. See example implementation in FIG. 12. Residual absorbance may be defined as an adjusted absorption after a melanin reduction scheme. Ideally, contrary to the choroid data in FIG. 12, if all effects of choroid and RPE melanin could be eliminated, the curves would show overlap at longer wavelengths. However, a higher overlap (especially at longer wavelengths) is observed with changing melanin concentrations in the RPE. This may be expected since RPE melanin has a more uniform effect on total absorbance as shown in FIG. 11.

Results.

The multi-aperture system with lenslet array was tested on eyes of healthy volunteers after dilation with Tropicamide Ophthalmic Solution (Akorn Inc, Buffalo Grove, Ill.) for about twenty minutes before testing, and imaging experiments were conducted very similarly to a clinical fundus exam. Although a fundus camera flash may also be used, a white light source was sufficient. Typical images divided by the multi-aperture system are shown in FIG. 13.

The multi-aperture system is able to simultaneously capture very large portions of the fundus in each image, but cropping of images may occur due to the limited size of the CCD when trying to maximize the imaging area, such as with a with a 10.2×8.3 mm size CCD. This issue may be solved, for example, with a larger CCD, such as a 36.1×24.0 mm CCD, which is commercially available.

Figure 13:
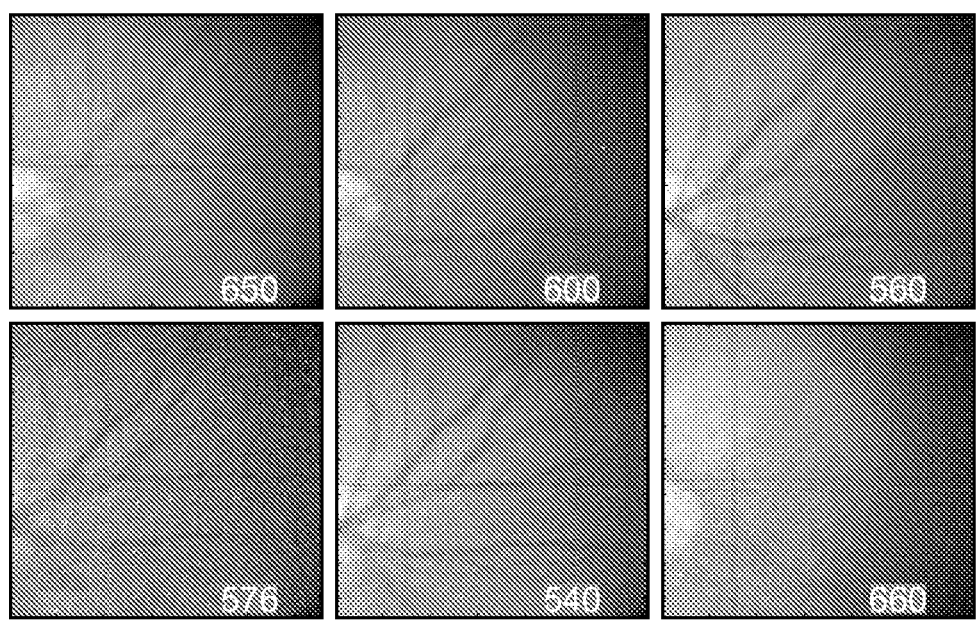
FIG. 13 is a set of wavelength-specific fundus images acquired with a multi-aperture system similar to embodiments of the present invention.

Each of the images in FIG. 13 shows different features. Images collected in the green region of the spectrum (e.g., 540, 560, and 576 nm) have high contrast in the vessel region due to the high hemoglobin absorbance, while the vessels are almost transparent in images collected with red filters (e.g., 650 and 660 nm). Differences in arterial and venous absorption are also noticeable.

After identifying arteries and veins in the images, a region of interest may be selected inside a vessel area ($R_{vessel}$) and in regions just next to the vessel ($R_{background}$). See white lines in FIG. 14. Pixel values captured on the vessel may then be normalized with values next to the vessel. Finally, optical density of the vessel region may be calculated:

$$OD(\lambda)=-\log_{10}[R_{vessel}(x,y,\lambda)/R_{background}(x,y,\lambda)] \quad (11)$$

Figure 14:
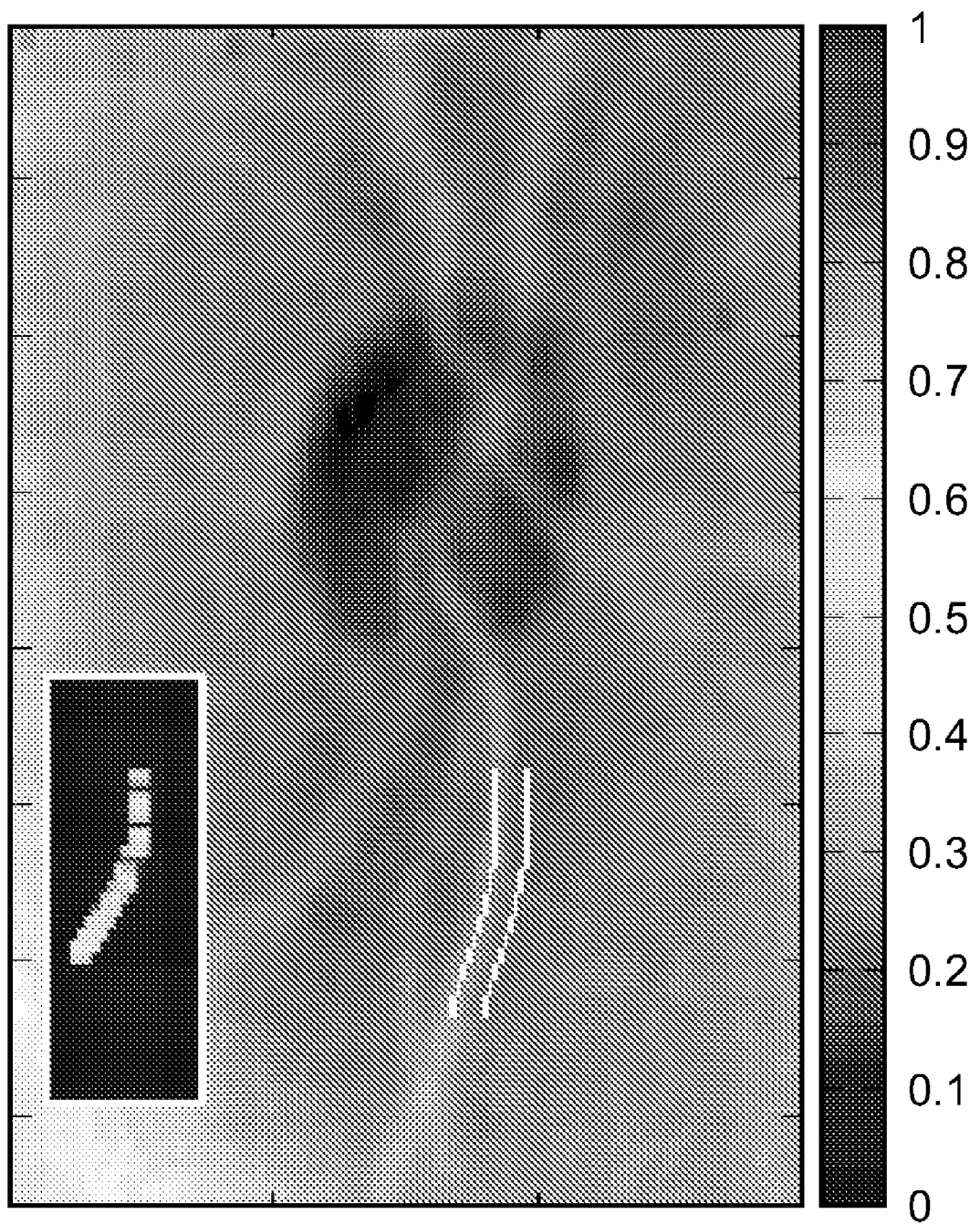
FIG. 14 is a D image of the retina of one volunteer from values obtained at 540, 560, and 580 nm with each value from a region of interest on a vessel indicated by white lines normalized by a corresponding value near the vessel and with the insert showing the calculated value of oxygen saturation on the large vessel according to the scale on the right.

The resulting data may be analyzed, for example, with the Delori model. An optical density or D image of the retina of a healthy volunteer is shown in FIG. 14. As shown in the insert, oxygen saturation ($SO_2$) values in the vein cluster between about 45% to 50% oxygen saturation, while $SO_2$ values from arteries generally cluster around 95%. Some intra-vessel variability was present in arteries and veins analyzed. However, this variability is not uncommon with reconstructed maps of $SO_2$. Further work may be needed to generate more uniform maps for complete fundus images.

Remarks.

A multi-aperture camera system for oxygen saturation measurement of the retinal vessel is described. The system is based on a lenslet array architecture and may have no moving parts and be interfaced with an optical device, such as a fundus opthalmoscope or slit lamp. As shown in examples, six spectroscopic sensitive images were collected in a single snapshot so that any impact of eye movement is greatly eliminated. Although resolution may be about 150 pixels×150 pixels in these examples, resolution may be improved with a larger CCD. Image quality may also be improved in these examples by replacing the focusing screen used to reduce the depth of field of the lenslets, with a more appropriate optical layout.

The system may be easily modified to accommodate different sets of filters and other optical elements. For example, polarizing optics may be included to reduce the effect of the eye melanin, to enhance the vessel to background contrast, and/or to observe foveal birefringence. In vitro tests have shown that a multi-aperture system may be able to measure oxygen saturation in a simplified model eye, and in vivo testing is consistent with previous reports.

Example 2

Light Transport in the Retinal Layers

The eye is composed of several layers, each different in structure, absorption and scattering properties. The optical properties of these layers affect the total amount of light reflected by the eye fundus as well as the spectral characteristics of the light. Effective models for the calculation of oxygen saturation in the retina attempt to compensate for the effects of various layers of the eye to ultimately isolate absorption due to superficial retinal vessels. Monte Carlo simulations may be used to model the behavior of light traveling through the retina. The impact of choroid melanin on a reflected beam of light as a function of wavelength, and the error in calculating oxygen saturation in superficial retinal vessels caused by choroid pigmentation may be evaluated.

Figure 15:
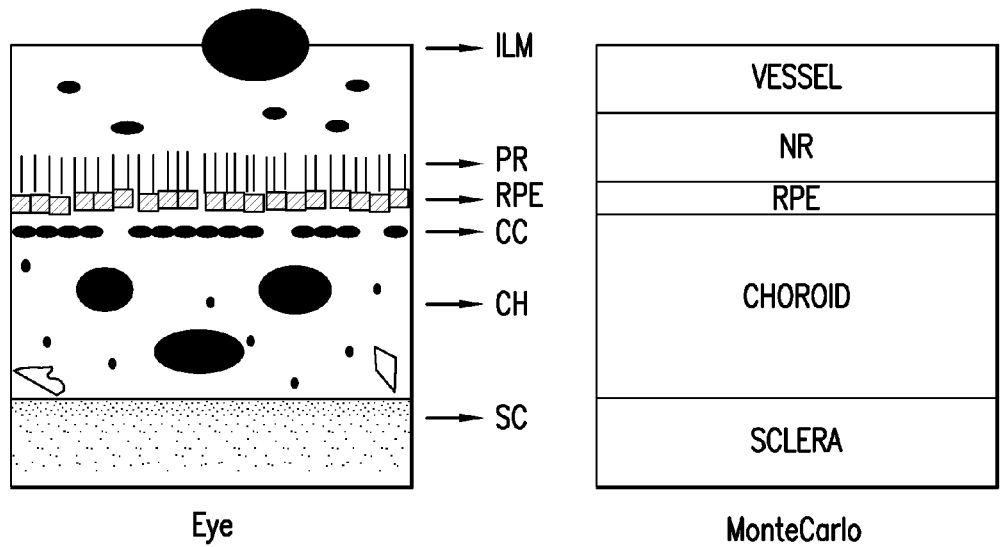
FIG. 15 is a schematic diagram showing the layers in the ocular fundus (left panel) simplified in Monte Carlo simulations (right panel).

In reference to FIG. 15, a depiction of the ocular fundus as well as a simplified representation that may be used in Monte Carlo simulations is provided. A retinal vessel may be as small as 10 μm and as large as 250 μm. Retinal vessels may be highly scattering due to the presence of erythrocytes, and absorbing because hemoglobin has a high extinction coefficient. The layer starting with the inner limiting membrane (ILM) and ending with the photoreceptors (PR) is the neural retina (NR), a layer that is about 200 μm thick and includes the photoreceptors. The retinal-pigmented epithelium (RPE) may be an approximately 10-μm thick-layer, and the main absorber in this layer is melanin. The choroid is a complex 250-μm-thick structure comprising large blood vessels, melanocytes, and connective tissues including collagen. Choriocapillaris (CC) and choroidal stroma (CH) are considered large layers of the choroid, where main absorbers include melanin and blood. Finally, the sclera may be about 700 μm thick and composed largely of collagen fibrils (type I and III) having little absorption.

Others have modeled light transport through the retina, such as by using the MCML program to show the impact of the various retina layers on the retro-reflected light. See, e.g., Hammer et al., (1995), supra; and Preece et al., (2002), supra. Hammer et al. measured optical properties of a cow retina using a double integrating sphere layout and then used these properties in Monte Carlo with doubling simulations. Preece et al. modeled four retina layers in their Monte Carlo simulations. They considered the neural retina, the choroids, the retinal pigment epithelium (RPE), and the sclera. They used Hammer's scattering coefficients ($\mu_s$) for all layers, reducing $\mu_s$ for the neural retina by about 25% of the value proposed in Hammer et al. to simulate human retina values. Tissue anisotropy (g) has been considered constant across all the wavelengths by most groups. This approximation may also be used in this example since g varies only by a few percentage points in the range of interest. The main absorbers in the retina are oxygenated and deoxygenated hemoglobin in the retina vessel and choroid, as well as melanin in the RPE and choroid. Values of melanin absorption coefficients are known. See, e.g., Anderson et al., "The optics of human skin," *J. Invest. Dermatol.*, 77:13-19 (1981), the entire contents and disclosure of which are hereby incorporated by reference.

Figure 16:
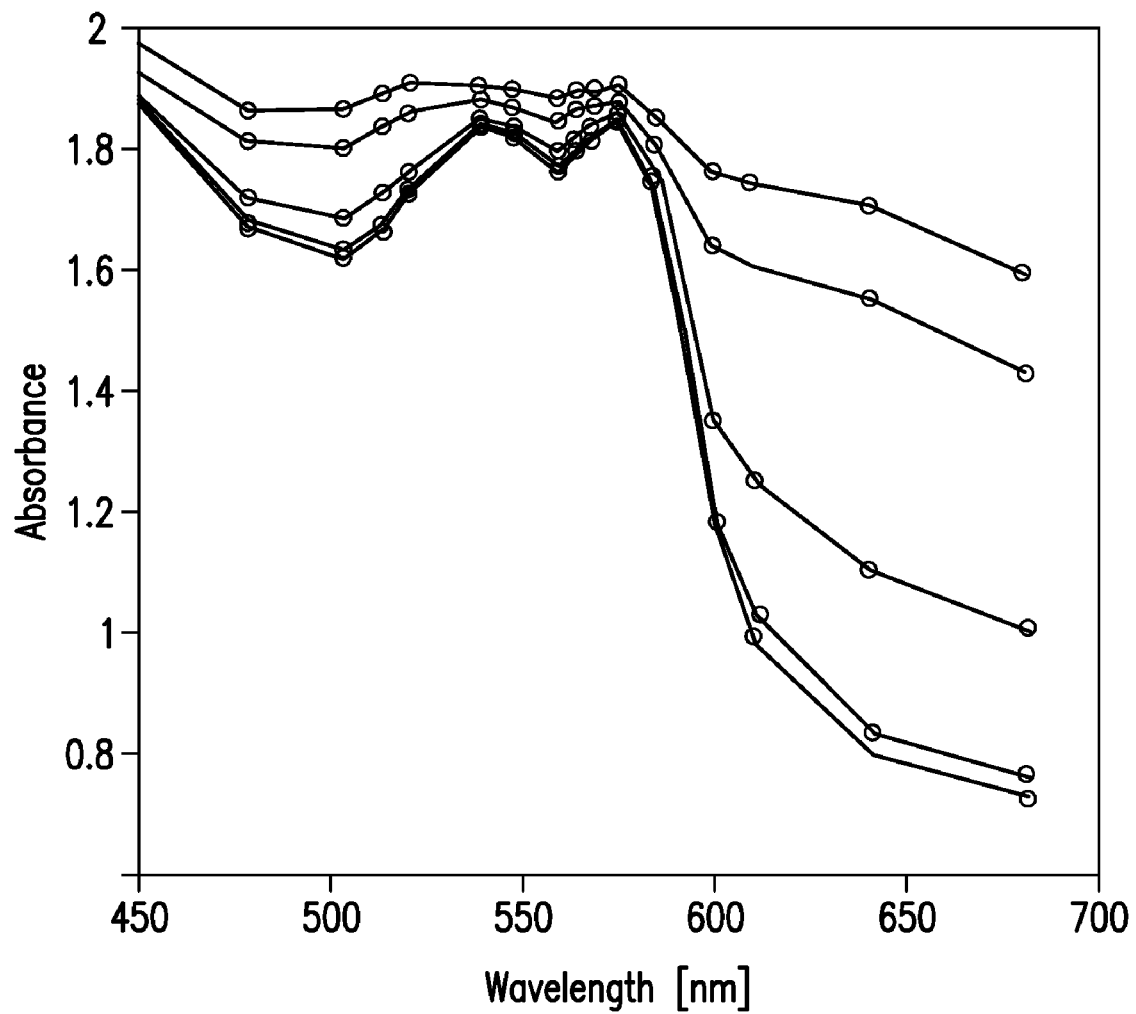
FIG. 16 is a plot of wavelength-dependent absorbance of melanin according to a Monte Carlo model when the amount of melanin in the choroid is increased from $0.001$ $mmol \cdot l^{-1}$ (bottom curve) to $10$ $mmol \cdot l^{-1}$ (top curve).

The extinction coefficients of Hb and $HbO_2$ are known and available at most visible wavelengths. The total absorption by the choroid is a result of both melanin and hemoglobin. The choroid is considered 95% oxygenated with a 70% blood volume fraction. Values of melanin concentration may vary depending on a patient's eye color and ethnicity. In simulations and as shown in FIG. 16, the melanin concentration may be varied from 0.001 to 10 mmol·$1^{-1}$ with blood content kept at aforementioned values. Choroid pigmentation has been shown to influence the total reflectance from the retina. RPE melanin concentration may be about 1 mmol·$1^{-1}$.

Four retina layers may be used in this simulation: the neural retina, the RPE, the choroid, and the sclera. All simulations may be conducted with MCML with 1 million photons. In this simulation, twenty different wavelengths uniformly distributed between 450 and 680 nm may be analyzed with optical properties the same as Wang et al., (1995), supra.

The impact of choroid melanin may be most visible at larger (green) wavelengths, and some have used reflectance values at these wavelengths for this reason. The RPE concentration may vary among different individuals but may be easier to eliminate because its effect is less wavelength-dependent compared to choroid melanin.

Figure 17:
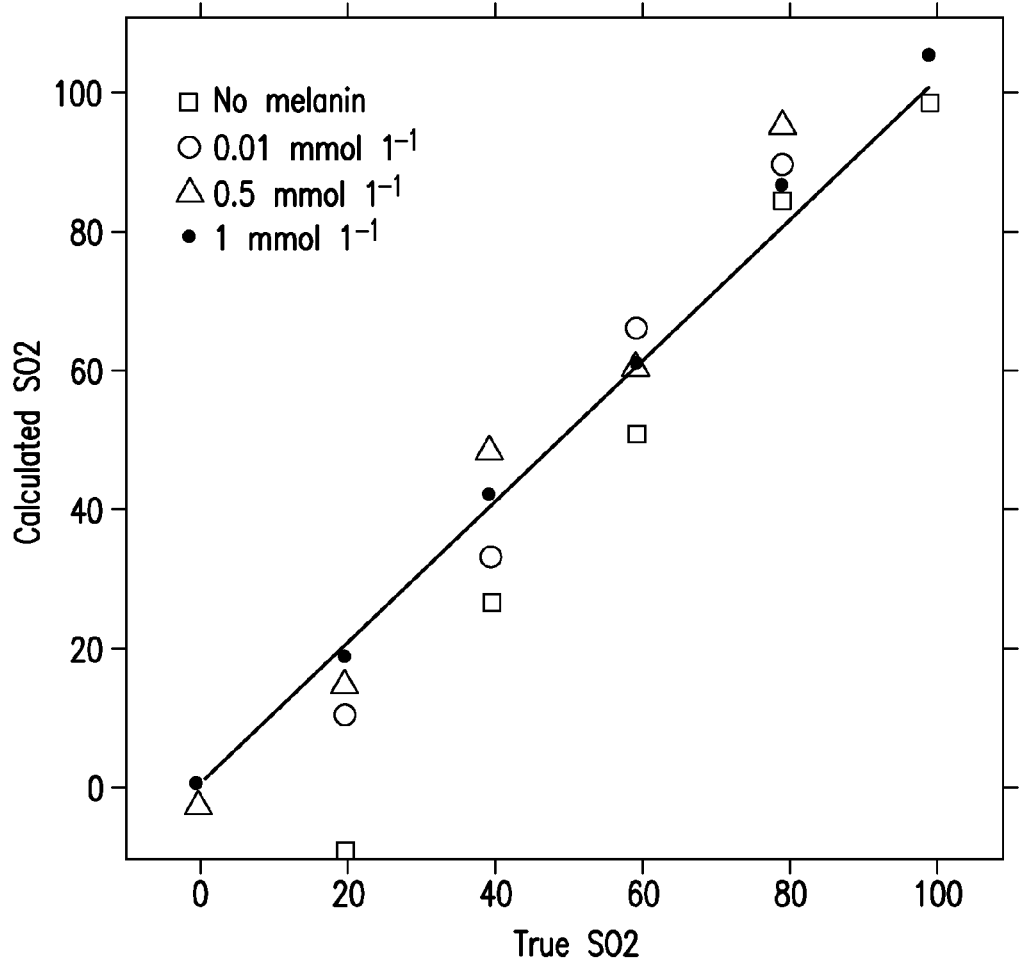
FIG. 17 is a plot of oxygen saturation in a 10 μm retinal vessel obtained with a three wavelength algorithm for four different amounts of choroidal melanin (square, open circle, triangle, filled circle).
Figure 18:
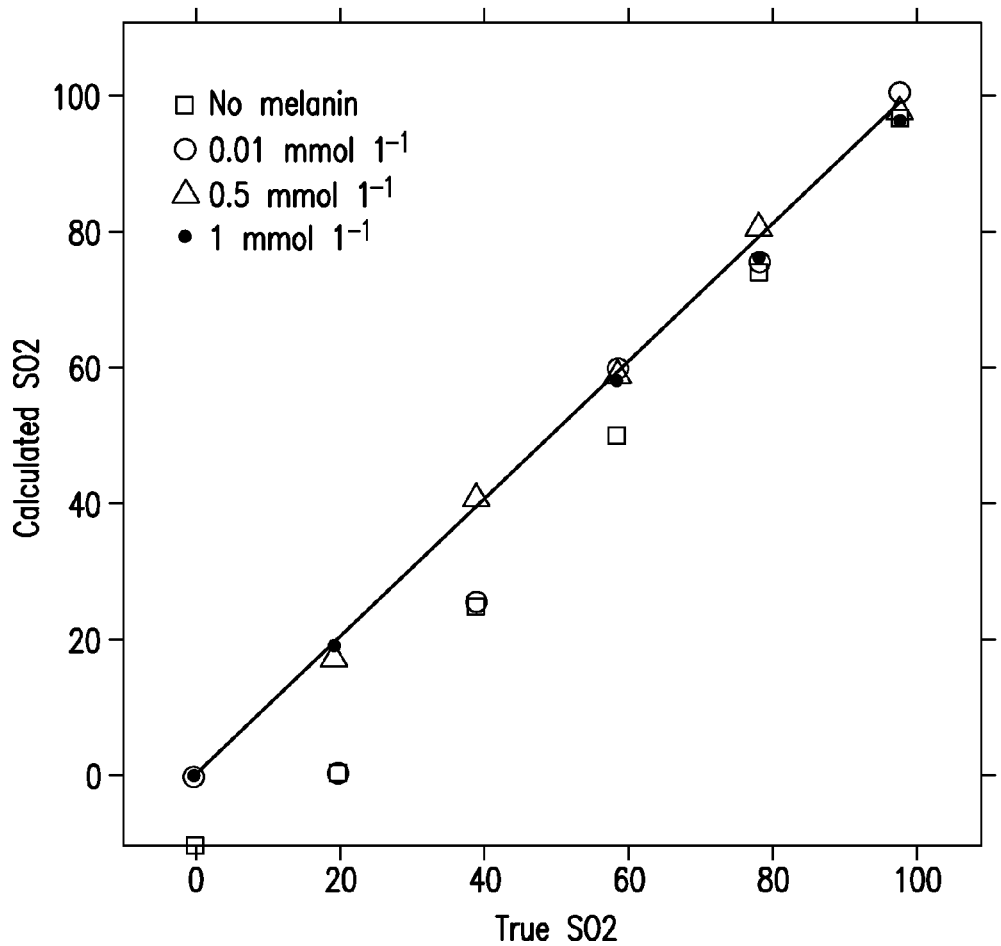
FIG. 18 is a plot of oxygen saturation in a 10 μm retinal vessel obtained with a multi-wavelength algorithm for four different values of choroidal melanin (square, open circle, triangle, filled circle).

In some simulations, the efficacy of two models for oxygen saturation in retinal top vessels in response to changes in choroidal melanin may be assessed. These algorithms may include: a three wavelength model by Delori or a multi-wavelength algorithm by Schweitzer et al. In one simulation, five retina layers, the four layers previously mentioned with the addition of a top vessel, may be used. To model optical properties of the vessel, values of whole blood measured by Gemert et al. may be used. See, e.g., Faber et al., "Oxygen saturation-dependent absorption and scattering of blood," *Phys. Rev. Lett.*, 93:028102-1-028102-4 (2004), the entire contents and disclosure of which are hereby incorporated by reference. In the calculation, the scattering coefficient (and the respective absorption coefficients) for oxygenated blood may differ from the one for deoxygenated blood. Anisotropy may be kept constant at 0.99, although it is known to vary between 0.993 and 0.998 across wavelengths of interest. Although the Henyey-Greenstein phase function used in MCML may not be optimal when describing light scattering from red blood cells, it provides a good approximation. Blood absorption in superficial vessels generally dominates scattering ($\mu_a$>>$\mu_s'$). Moreover, the simulations may be conducted on a retinal vessel with a diameter of about 10 μm so that less than one scattering event occurs within vessel boundaries. Although inclusion of the neural retinal layer may seem redundant, the measurement of the neutral retina (NR) layer does not always include retinal vessels, and the values of absorption in this layer are several orders of magnitude smaller than expected for blood. Therefore, the effect of this NR layer may be excluded in some modeling experiments. Simulations conducted on a 10 μm vessel are shown in FIGS. 17 and 18 with simulations conducted on larger vessels showing similar behavior.

Oxygen saturation in the top retinal vessel may be varied between 0 and 100%. The simulations may be conducted for different values of choroidal melanin concentrations. The reflectance values may be obtained with the five-layer model $I_{ves}$ normalized by values obtained without the vessel $I_{std}$. This may mimic what is commonly done experimentally, where reflectance data on a vessel is normalized by reflectance values near the vessel. A three-wavelength algorithm proposed by Delori et al. may be tested with oxygen saturation obtained by the following equation:

$$SO_2 = \frac{[D^{\lambda 1}(\varepsilon_{Hb}^{\lambda 3} - \varepsilon_{Hb}^{\lambda 2}) + D^{\lambda 2}(\varepsilon_{Hb}^{\lambda 1} - \varepsilon_{Hb}^{\lambda 3}) + D^{\lambda 3}(\varepsilon_{Hb}^{\lambda 2} - \varepsilon_{Hb}^{\lambda 1})]}{D^{\lambda 1}[(\varepsilon_{Hb}^{\lambda 3} - \varepsilon_{HbO_2}^{\lambda 3}) - (\varepsilon_{Hb}^{\lambda 2} - \varepsilon_{HbO_2}^{\lambda 2})] +} \quad (12)$$
$$D^{\lambda 2}[(\varepsilon_{Hb}^{\lambda 1} - \varepsilon_{HbO_2}^{\lambda 1}) - (\varepsilon_{Hb}^{\lambda 3} - \varepsilon_{HbO_2}^{\lambda 3})] +$$
$$D^{\lambda 2}[(\varepsilon_{Hb}^{\lambda 2} - \varepsilon_{HbO_2}^{\lambda 2}) - (\varepsilon_{Hb}^{\lambda 1} - \varepsilon_{HbO_2}^{\lambda 1})]$$

where D=−log 10($I_{ves}/I_{std}$), and $\epsilon_{HbO2}$ and $\epsilon_{Hb}$ are known values of extinction coefficients for oxygenated and deoxygenated hemoglobin. Results obtained with the three-wavelength algorithm are shown in FIG. 17.

The three wavelength algorithm is able to reconstruct the true values of oxygen saturation of the outer retinal vessel with only some error. At low $SO_2$ values, however, the error appears large, and low choroidal melanin concentrations also show significant error. Experimentally high levels of melanin in the choroid may lead to higher error due to the low level of light back-reflected from the retina. In simulations, the presence of melanin in the choroid may attenuate the effect of blood absorption and scattering in that layer.

The multi-wavelength model introduced by Schweitzer is particularly effective when a larger number of wavelengths are available. The algorithm keeps into account not only the hemoglobin absorption, but also the wavelength-dependent scattering of erythrocytes. The optical density of light back-scattered from a vessel may be modeled as:

$$D(\lambda) = B + n\log\left(\frac{1}{\lambda}\right) + b[\varepsilon_{Hb}(\lambda) + s(\varepsilon_{HbO_2}(\lambda) - \varepsilon_{Hb}(\lambda))]c_{tot}l \quad (13)$$

where the first two terms B and n log(1/λ) are used to simulate both wavelength-independent and wavelength-dependent scattering. The term s is an experimental geometry factor, $c_{tot}$ is the total hemoglobin concentration, and $l$ is the vessel thickness.

A least squares mechanism using the Nelder-Mead simplex method may be used in combination with four fitting parameters (B, $A=c^{tb}_{tot}$, s, and n). See, e.g., Nelder et al., (1965), supra. Results obtained with this model using multiple (14) wavelengths uniformly distributed between 450 nm and 700 nm are shown in FIG. 18. This algorithm is effective at capturing true values of oxygen saturation in the retina vessel, although better results may be obtained when some melanin is present in the choroid and when higher $SO_2$ values are present. A minimization technique, such as for the multi-wavelength algorithm, may be dependent on initial values and time-consuming, but this type of algorithm may offer more useful information regarding eye structure in assessing retina spatial variability.

Multi-Aperture Camera

1. Fundus Spectral Imager

An experimental multi-aperture system apparatus for the measurement of oxygen saturation in the retina is provided. The system may be based on a fundus camera (TRC-FET, Topcon Paramus, N.J.). Optical devices, such as fundus cameras, retinal cameras, ophthalmoscopes, or slit lamps, are common instruments in ophthalmic clinics to provide a magnified view of a patient's retina. The normal imager in a fundus system may be replaced with a multi-aperture system containing a lenslet array that is associated with a detection system, such as a CCD camera, so that several (e.g., six) retinal images may be collected in a single snapshot. An exemplary layout of a multi-aperture system is shown in FIG. 3. The optical device may contain a xenon lamp continuous light source and/or a flash that may be triggered by a multi-aperture system or camera. A dc light source may be used. The multi-aperture camera may be attached at the exit pupil of an optical device in place of the usual camera. Images may be collected in a dark room.

2. Six-Lens Camera System

In this example, a multi-aperture system may be based on a six-lens array. The system containing a lenslet and filter array may be associated with a detection system, such as a 10 bit monochromatic digital camera (Lumenera, North Andover, Mass.). The size of a CCD camera may be about 10.2 mm×8.3 mm with 1392 pixels×1040 pixels. The lenslet array may be custom built with a plurality of lenslets, such as six plano-convex lenses (LightPath Optical Instrumentation, Shanghai, China) supported by a solid matrix, such as an aluminum plate. The lenses may be about 2 mm in diameter and have an aperture equal to about 0.15 with an effective focal length of about 5 mm. Lens to lens separation may be about 2.5 mm. Bandpass filters (e.g., 20 nm full-width at half maximum (FWHM), Newport, Irvine, Calif.) may be arranged in a layout similar to the lenslet array. Each filter may be about 2.5 mm×2.5 mm, but the 575 nm filter may be circular with about 3 mm diameter. Different combinations of filter arrays may be tested including the quintuplet (540, 560, 576, 600, and 680 nm) and sextuplets (560, 575, 600, 630, 650, and 660 nm or 540, 560, 575, 600, 650, and 660 nm). Filters may be positioned at about 0.2 mm from the lenses. FIG. 4 provides an illustration of the concept of image multiplication achieved with the lenslet array of the multi-aperture system. The letter F is shown projected onto a detection surface of a (CCD) camera through six equally spaced lenses. Images obtainable with this system allowing for registration may be limited to about 300 pixels×300 pixels depending, for example, on the size of a CCD. Higher resolution images may be especially desired when observing small retina capillaries.

3. 18-Lens Camera System

Figure 19:
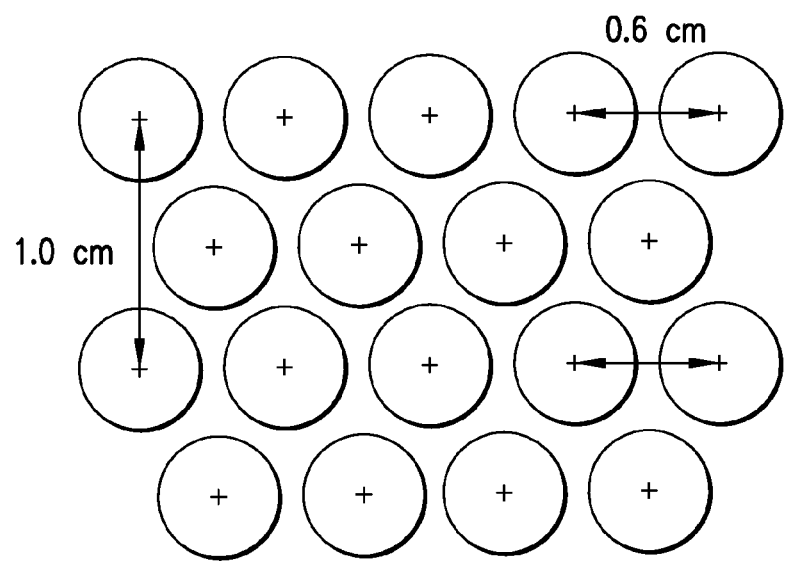
FIG. 19 is a schematic diagram of a lens layout for an 18-lenslet array that may be used for a larger format camera according to embodiments of the present invention.

When using models for $SO_2$ calculation that consider the optical properties of the retina, such as in Schweitzer et al., a larger number of wavelength-specific images are generally desired. A multi-aperture imaging system is proposed that may accommodate a large number of lenslets positioned in an array to generate larger numbers of separate images (e.g., eighteen) on a detection device, such as a single CCD camera. The system may use a larger CCD camera, such as a 12 b monochromatic digital camera (Lumenera, North Andover, Mass.) that is 36.1 mm×24.0 mm having 4008 pixels×2672 pixels. A lenslet array may be arranged to maximize the area of each image or sub-image. An example of a lenslet array or layout with 18 lenses is shown in FIG. 19. In this example, each lens may be about 0.6 cm center to center in the horizontal direction and about 1 cm in the vertical direction. Multielement glass lens (Sunex, Carlsbad, Calif.) with a focal length of about 5.9 mm may be used in this system. The lenses may be encased in a black plastic support. A filter array having similar layout may be positioned in front of the lenslet array. For example, the filter array may be composed of 14 color filters (20 nm FWHM, Newport, Irvine, Calif.), three polarizers (Edmund Optics, Barrington, N.J.), and one neutral density filter (OD=0.3, Edmund Optics, Barrington, N.J.).

The color filters may be, for example, 460, 480, 500, 520, 530, 540, 560, 580, 590, 600, 620, 630, 640, and 660 nm. Three of the polarizers may be oriented at 0°, 45°, and 90° to the source polarization. By combining images obtained with the three polarizers and the ND filter, the first three terms of the Stokes vector may be obtained. In addition, a quarter wave plate and linear polarizer may also be used in tandem to determine circularly polarized light to provide the fourth term of the Stokes vector. The Stokes vector may provide insight into structural features of the eye.

Figure 20:
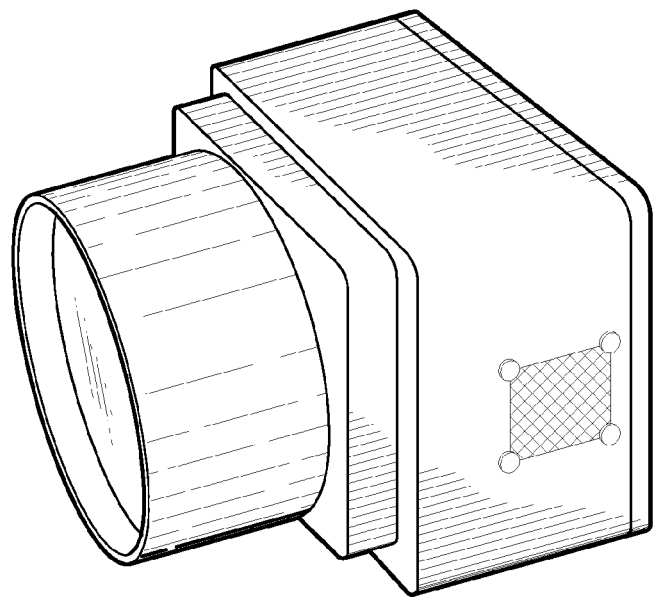
FIG. 20 is a perspective view of a larger format multi-aperture camera according to embodiments of the present invention.

To minimize the effect of lens parallax on the resulting image, two large (e.g., diameter=6 cm) magnifying lenses (e.g., f=150 mm) may be positioned in front of the filter and lenslet arrays. The system may also be enclosed in a black anodized aluminum case. An example image of a complete imager is shown in FIG. 20.

By using this combination, the multi-aperture system focal length may be about 3 cm and the field of view about 3 cm×3 cm. Images obtained with this system may be about 600 pixels×600 pixels.

4. Systems Calibration

Figure 21:
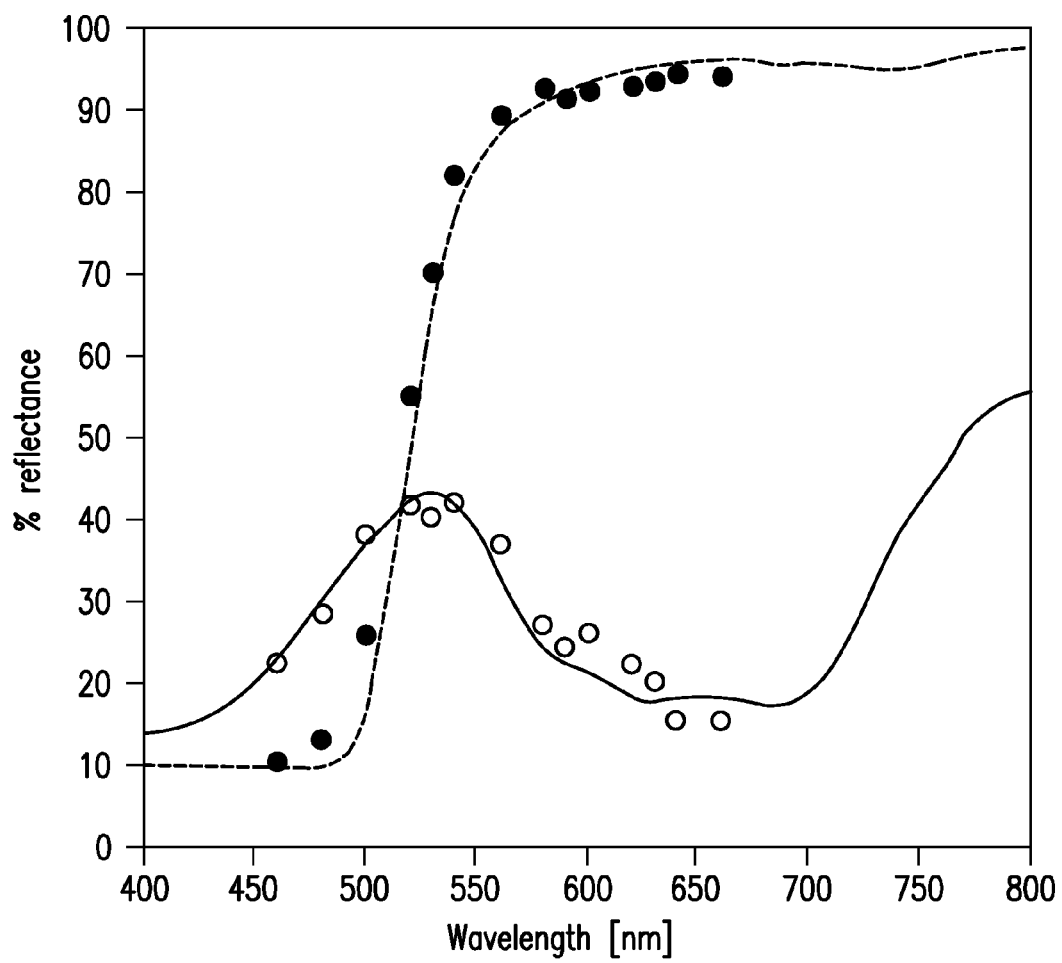
FIG. 21 is a plot of the normalized reflectance from color standards obtained using an 18 lenslet array (with only 14 color filters used).

Both camera spectral responses may be tested with the aid of colored standards, such as National Institute of Standards and Technology (NIST) traceable Spectralon standard (Labsphere, North Sutton, N.H.). The standards may be green and yellow. Images of the standard may be captured with the multi-aperture system, and normalized using a 90% reflectance standard that may also be NIST traceable. Results obtained with an eighteen-lenslet system are shown in FIG. 21. In FIG. 21, filled symbols are experimentally obtained values from reflectance of a green standard normalized by a 90% reflectance standard, the dashed line corresponds to calibrated reflectance values for the green standard provided by the manufacturer, open symbols are experimentally obtained values from normalized reflectance of a yellow standard, and the solid line corresponds to calibrated reflectance values for the yellow standard provided by the manufacturer.

Figure 22:
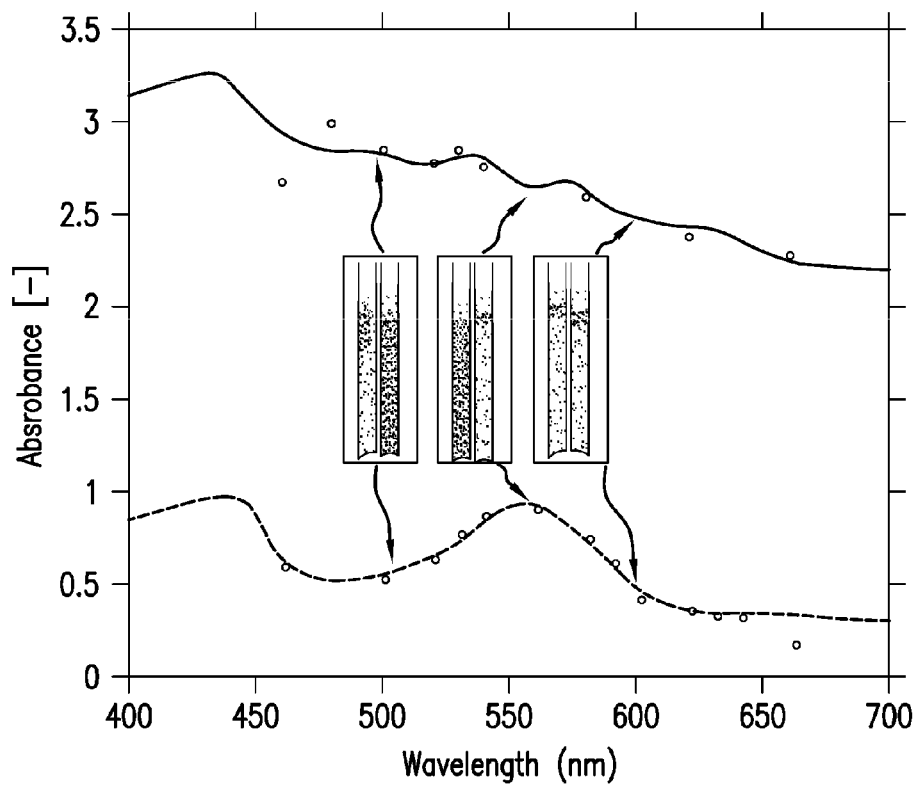
FIG. 22 is an absorption plot of bovine hemoglobin comparing values obtained using a multi-aperture camera versus a bench-top spectrophotometer.
Figure 23:
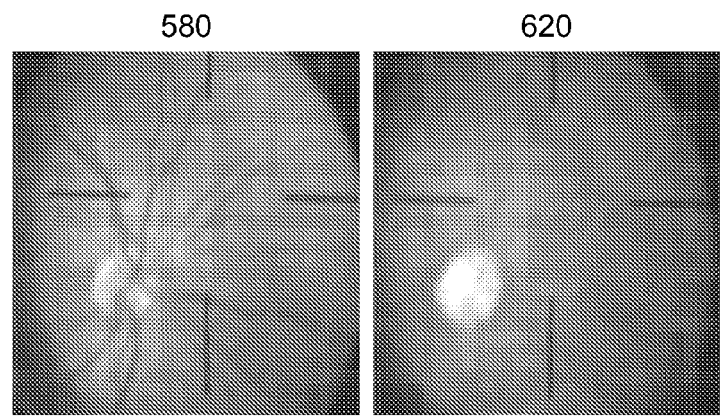
FIG. 23 is a pair of images obtained with a larger format camera showing differences in absorbance of retinal vessels at 580 nm (vessels clearly visible) and 620 nm (vessels not visible due to low hemoglobin absorption).

The six-lenslet system in the example above gave similar results. The system may also be used to measure reflectance from a solution of hemoglobin. A total of about 25 mg of bovine hemoglobin (Sigma, St. Louis, Mo.) may be dissolved in about 200 mL of water and left in open air for several minutes to allow the hemoglobin to completely dissolve and bind with oxygen. The liquid may assume a brownish red color and then be stored in a 1-cm-thick plastic cuvette. The absorbance of a hemoglobin filled cuvette may be measured with a bench-top spectrophotometer (e.g., Ultrospec 3000, Pharmacia Biosystems, DK). Typical curves for oxyhemoglobin may be obtained as shown in FIG. 22. Half of the mixture may then be combined with 5 mg of sodium hydrosulfite (Sigma, St Louis, Mo.) and stored in a 1-cm-thick plastic cuvette. Sodium hydrosulfite is a reducing agent that may be used to deoxygenate the hemoglobin solution. The cuvette may be sealed to avoid hemoglobin recombination with oxygen. The mixture may be measured with the spectrophotometer showing a typical deoxyhemoglobin absorption curve as shown in FIG. 22. Finally, both cuvette may be positioned at about 3 cm from the multi-aperture system.

A white led source (Throlabs, Newton, N.J.) may be positioned behind the cuvettes facing the imager, and a diffuser added between the cuvettes and the light source. Fourteen wavelength sensitive images of light transmitting through the cuvette may be obtained in a single snapshot through the use of filters. In the inset of FIG. 22, three of such images for deoxygenated and oxygenated hemoglobin at 500, 560, and 600 nm are shown with the left cuvette containing deoxygenated hemoglobin and the right cuvette containing oxygenated hemoglobin. Two 100×100 pixels regions may be selected on each image, one on the cuvette containing oxygenated hemoglobin and one on the cuvette containing deoxygenated hemoglobin. FIG. 22 provides a comparison of absorption values for bovine hemoglobin obtained using a multi-aperture camera or a spectrophotometer. In FIG. 22, the circles correspond to values obtained by averaging a region of interest in the cuvette images for deoxygenated or oxygenated hemoglobin. On the other hand, absorption lines correspond to deoxygenated (lower curve) or oxygenated (upper curve) hemoglobin with the upper oxyhemoglobin curve shifted +2 for clarity. Values obtained using either the multi-aperture system or spectrophotometer showed strong agreement.

The average value of transmission (T) through such regions may be calculated and then transformed into absorbance (A) values using the equation:

$$A = -\frac{1}{L}\log_{10}(T) \quad (14)$$

where L is the cuvette thickness (1 cm). The results may be compared with spectrophotometer measurements. Both curves may be normalized by their maximum value. The curves and values measured with the spectrophotometer and obtained with the multi-aperture system, respectively, generally show agreement. Similar experiments may also be conducted with the six-lenslet system using cuvettes as well as a simplified model of the human eye. The data may also be modeled with both the Delori and Schweitzer algorithms, and values of oxygen saturation obtained with an associated error of about 10%.

Results

Both of the six- and eighteen-lenslet systems in these examples may be tested on the eyes of healthy volunteers according to a typical procedure of a clinical fundus exam. Oxygen saturation values on selected vessels of the retina may then be obtained using the Schweitzer algorithm. Arteries and veins may be identified on the images, and regions of interest may be selected on a vessel area ($R_{vessel}$) and in regions in close proximity to the vessel ($R_{background}$). Average pixel values captured on a vessel may be normalized by values from the background next to it. The optical density of the vessel region may be calculated as:

$$OD(\lambda) = -\log_{10}\left(\frac{R_{vessel}(x, y, \lambda)}{R_{background}(x, y, \lambda)}\right) \quad (15)$$

Average values of oxygen saturation were observed to be about 95% for arteries and about 54% for veins. Although the large-format camera allows for the collection of more data points than the six-lenslet system, a similar level of variability in measurements was observed in these examples. Values of oxygen saturation varied as much as 10% across the same vessel depending on its position. Part of the variability may be due to non-uniformity of the eye absorber. A more accurate model may be necessary to capture the complex eye structure. The ability of the present multi-aperture system to view a large number of wavelength (and polarization) images of the retina of a subject in a single snapshot using a lenslet array may help to generate more data needed to model the complexities of the eye.

Remarks.

The multi-aperture system allows for the spectroscopic and spatial division of a fundus image. The system may be particularly suited for imaging the eye because of its ability to collect all images in a single snapshot to eliminate issues with eye movement. Projecting images onto a CCD necessarily decreases the resolution of each image. However, using a large-format camera, a greater number of images (e.g., 18 or as many as 24 with current technology) may be collected. Unfortunately, larger format CCDs are still relatively expensive and slow to operate.

It is challenging to calculate an accurate oxygen saturation value due to the complexities of the structure of the eye. The presence of melanin in the choroids impacts the calculation of oxygen saturation in both the Delori and Schweitzer models. The multi-aperture system described herein shows promise for investigating and developing parametric models for light travel in the retina because of the ability to simultaneously generate a large number of two-dimensional images corresponding to the same location within the retina for a variety of wavelengths and polarization states.

For discussion of possible embodiments of the present invention, see, e.g., Ramella-Roman et al., "A lenslet-based device for measuring oxygen saturation in the retina," *Proc. Of SPIE, Ophthalmic Technologies XVII* 6426:64261J-1-64261J-5 (2007); Ramella-Roman et al., "Spectroscopic Measurements of Oxygen Saturation in the Retina," *IEEE Journal of Selected Topics in Quantum Electronics* 13(6): 1697-1703 (2007); and Ramella-Roman et al., "Measurement of oxygen saturation in the retina with a spectroscopic sensitive multi aperture camera," *Optics Express* 16(9): 6170-6182 (2008), the contents and disclosure of which are hereby incorporated by reference in their entirety.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method, comprising the following steps:
   (a) placing an eye of a subject at an entrance pupil of an optical device; and
   (b) detecting a plurality of two-dimensional images of light reflected by the retina of the eye of the subject using a multi-aperture system attached to an exit pupil of the optical device, the multi-aperture system comprising:
   a lenslet array;
   a filter array; and
   a detection system for detecting light passing through said lenslet array and said filter array,
   wherein said lenslet array comprises at least seven lenses;
   wherein said filter array comprises a solid matrix having at least seven openings, at least three different wavelength filters, and at least two linear polarizers oriented at different angles, wherein each of the wavelength filters are associated with a respective one of said openings of said filter array, and wherein each of the linear polarizers are associated with a respective one of said openings of said filter array;

wherein said lenslet array is positioned closer than said filter array to said detection system;

wherein said filter array and said lenslet array of said multi-aperture system are positioned to generate at least seven separate and simultaneous two-dimensional images of light reflected by a retina of an individual projected onto a detection surface of said detection system by passing the reflected light through said filter array and said lenslet array with each image corresponding to approximately the same space or area of the retina of the individual, wherein an incident light is reflected by the retina of the individual to produce the reflected light, and wherein each two-dimensional image projected onto the detection surface of said detection system is generated by passing the reflected light through one of said openings of said filter array and a respective one of said lenses of said lenslet array; and wherein two of the two-dimensional images are each generated by passing the reflected light through one of the linear polarizers, and wherein three of the two-dimensional images are each generated by passing the reflected light through one of the wavelength filters.

2. The method of claim 1, wherein the step (b) of detecting a plurality of two-dimensional images is carried out by using a detection system.

3. The method of claim 1, wherein the optical device is a fundus opthalmoscope.

* * * * *